United States Patent [19]
Campbell et al.

[11] Patent Number: 4,489,075
[45] Date of Patent: Dec. 18, 1984

[54] CYCLIC SULFONAMIDOALKYL SUBSTITUTED 4-PIPERIDINOQUINAZOLINE CARDIAC STIMULANTS

[75] Inventors: Simon F. Campbell, Deal; David A. Roberts, Sandwich; John K. Stubbs, Deal, all of England

[73] Assignee: Pfizer Inc., New York, N.Y.

[21] Appl. No.: 489,271

[22] Filed: Apr. 27, 1983

[30] Foreign Application Priority Data

May 15, 1982 [GB] United Kingdom ................. 8214206

[51] Int. Cl.³ .................... C07D 417/14; A61K 31/54; A61K 31/505; A61K 31/445
[52] U.S. Cl. .................................... 424/246; 424/251; 544/3; 544/8; 544/284; 544/293

[58] Field of Search ....................... 544/293, 284, 8, 3; 424/251, 246

[56] References Cited

U.S. PATENT DOCUMENTS 3,971,783  7/1976  Barnish et al. ............... 260/256.4 Q
4,001,422  1/1977  Danilewicz et.al. ................ 424/251
4,188,391  2/1980  Campbell et al. .................... 424/251

Primary Examiner—John M. Ford
Attorney, Agent, or Firm—Charles J. Knuth; Peter C. Richardson; Gezina Holtrust

[57] ABSTRACT 6,7-Dialkoxy-4-[4-(cyclic-sulfonamidoalkyl)-piperidino]quinazolines and method of use as cardiac stimulants.

25 Claims, No Drawings

CYCLIC SULFONAMIDOALKYL SUBSTITUTED 4-PIPERIDINOQUINAZOLINE CARDIAC STIMULANTS

BACKGROUND OF THE INVENTION

This invention relates to piperidinoquinazolines which are phosphodiesterase inhibitors and cardiac stimulants of which a preferred class selectively increase the force of myocardial contraction without producing significant increases in heart rate. The compounds are useful in the curative or prophylactic treatment of cardiac conditions, in particular heart failure.

Quinazolines are a well-known class of organic compounds, some of which are reported to have useful therapeutic properties. U.S. Pat. No. 3,517,005 discloses 4-aminoquinazoline derivatives with hypotensive and bronchodilator activity, and U.S. Pat. No. 3,511,836 reports hypotensive activity for 2,4-diaminoquinazolines. Scarborough et al., J. Org. Chem., 27, 957 (1967) reports the preparation of several 4-(1-substituted-3-pyrrolidinylmethylamino)quinazolines. U.S. Pat. No. 3,971,783 discloses various 4-(heteroarylalkylamino)-quinazolines as cardiac stimulants. U.S. Pat. Nos. 4,001,422 and 4,188,391 disclose various cardiac stimulating 4-(heteroaryl)quinazolines, including certain 4-[4-(alkanesulfonamido)piperidino]quinazolines and 4-[4-(alkanesulfonamidoalkyl)piperidino]quinazolines.

SUMMARY OF THE INVENTION

According to the invention there are provided novel quinazoline compounds of the formula:

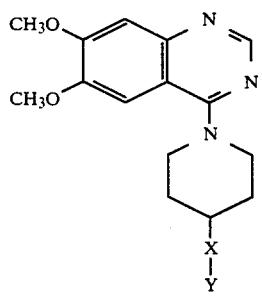

(I)

and their pharmaceutically acceptable salts;
wherein X is a straight or branched chain alkylene group having a total of from 1 to 4 carbon atoms; and Y is a group of the formula:

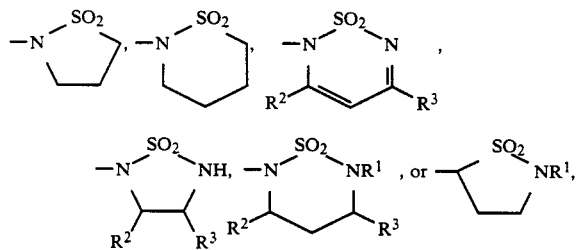

where
R¹ is H or $C_1$–$C_4$ alkyl; and
R² and R³ are each independently H or $CH_3$.
Preferably X is —$CH_2$—, —$(CH_2)_2$—, —$(CH_2)_3$—, —$CH(CH_3)$—, —$CH(C_2H_5)$—, —$CH(CH_3)CH_2$—, —$CH_2CH(CH_3)$— or —$CH(CH_3)CH_2CH_2$—.

$C_3$ and $C_4$ alkyl groups can be straight or branched chain.

Most preferably X is —$(CH_2)_2$—.

Y is preferably

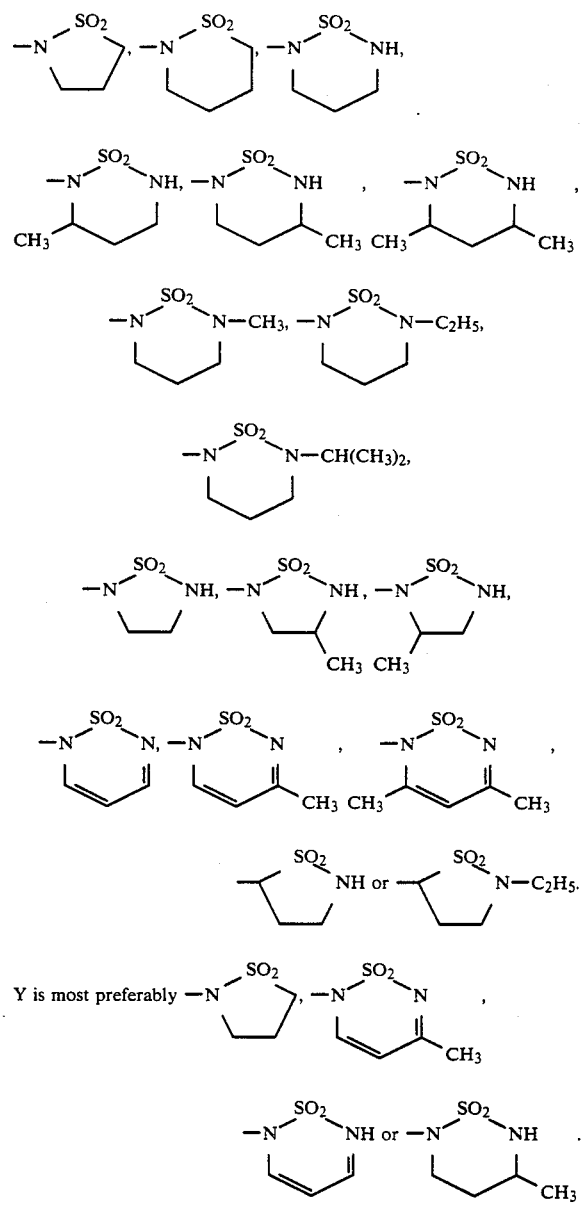

Y is most preferably

The most preferred individual compounds have the formula:

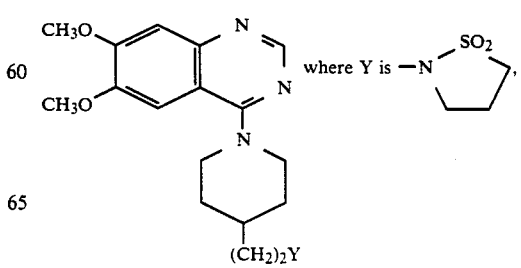

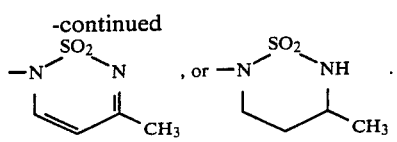

The pharmaceutically acceptable salts of the compounds of the formula (I) are preferably acid addition salts formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate and p-toluenesulphonate salts. The hydrochloride salts are preferred.

The cardiac stimulant activity of the compounds of the formula (I) is shown by their effectiveness in one or more of the following tests: (a) increasing the force of contraction in the isolated, spontaneously beating, guinea pig double atria or kitten right and left atria preparations; (b) increasing myocardial contractility (left ventricular dp/dt max.) in the anaesthetised cat or dog with a left ventricular catheter; (c) increasing myocardial contractility in the conscious dog with an implanted left ventricular transducer (dp/dt max.) of an exteriorised carotid artery loop (systolic time intervals).

In test (a) the positive inotropic and chronotropic responses of the atria to the test compound are measured at several doses and compared with the responses elicited by isoprenaline. The comparison of the dose response curves obtained gives a measure of the force versus rate selectivity of the test compound.

In test (b) the positive inotropic action of the test compound following intravenous administration is measured in the anaesthetised cat or dog. The magnitude and duration of this action, and the selectivity for increase in force versus frequency of contraction of the test compound are obtained, as are its peripheral effects, e.g. the effect on the blood pressure.

In test (c) the positive inotropic action of the test compound following intravenous or oral administration to a conscious dog with an implanted left ventricular transducer (dp/dt max.) or an exteriorised artery loop (systolic time intervals) is measured. The magnitude of the inotropic action, the selectivity for increase in force versus frequency of contraction, and the duration of action of the inotropic effect of the test compound are all obtained.

The compounds of the formula (I) can be administered alone but will generally be administered in admixture with a pharmaceutical carrier selected with regard to the intended route of administration and standard pharmaceutical practice. For example they are administered orally in the form of tablets containing such excipients as starch or lactose, or in capsules either alone or in admixture with excipients, or in the form of elixirs or suspensions containing flavouring or colouring agents. When administered parenterally, for example, intravenously, intramuscularly or subcutaneously, they are best used in the form of a sterile aqueous solution which may contain other solutes, for example, enough salts or glucose to make the solution isotonic.

For administration to man in the curative or prophylactic treatment of cardiac conditions such as congestive heart failure, the daily oral dosages of the compounds of the invention are from 10 mg to 1 g daily, taken in 2 to 4 divided doses per day, for an average adult patient (70 kg). Dosages for parenteral administration, typically by intravenous infusion, are from 1 to 700 mg per day for a typical adult patient, for example in the treatment of acute heart failure. Thus for a typical adult patient, individual tablets or capsules will typically contain from 10 to 250 mg of active compound, in a suitable pharmaceutically acceptable vehicle or carrier.

Thus the present invention provides a pharmaceutical composition comprising a compound of the formula (I) as defined above or pharmaceutically acceptable acid addition salt thereof together with a pharmaceutically acceptable diluent or carrier.

The invention also provides a method of stimulating the heart of an animal, including a human being, which comprises administering to the animal a compound of the formula (I) or salt thereof as defined above, in an amount sufficient to stimulate the heart of the animal.

The invention yet further provides a compound of the formula (I) or pharmaceutically acceptable acid addition salt thereof, for use in treating an animal, including a human being, to stimulate the heart of the animal.

DETAILED DESCRIPTION OF THE INVENTION

The compounds of the invention are prepared by a number of routes:

Route A

This method for preparing compounds is illustrated as follows:

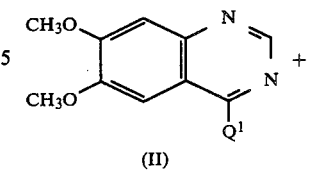

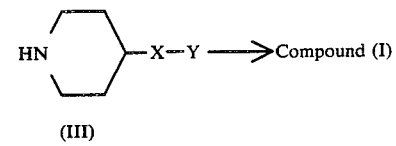

$Q^1$ is an appropriate facile leaving group such as Cl, Br or I.

$Q^1$ is preferably Cl.

The reaction is typically carried out in an organic solvent, e.g. ethanol, with heating at up to reflux temperature, for 2–15 hours. When $Q^1$ is Cl, Br or I, the presence of an non-nucleophilic base, e.g. a tertiary amine base such as triethylamine, is advantageous. The product can be isolated and purified by conventional procedures. An acid addition salt form of (III) can be used as the starting material although a base is preferably then present to neutralise the acid.

The starting materials of the formula (III) are either known compounds or can be prepared by conventional procedures, typically by the hydrogenation of the corresponding pyridines using hydrogen/PtO$_2$ under acidic conditions at 50°–60° C. and 50–60 p.s.i. until hydrogen uptake ceases, e.g. after 4–8 hours.

Typical routes to these pyridines (and piperidines in route [j]), many of which are illustrated in detail in the following Preparations, are as follows:

(a)
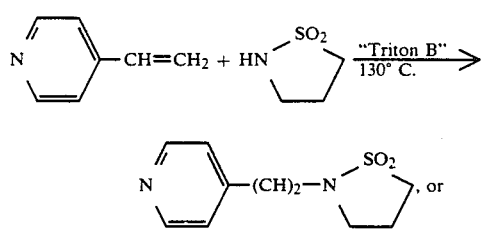
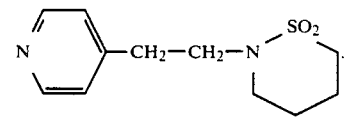
If a substituted alkylene chain is required then the vinyl group should be appropriately substituted by $CH_3$ or $C_2H_5$.
(b)
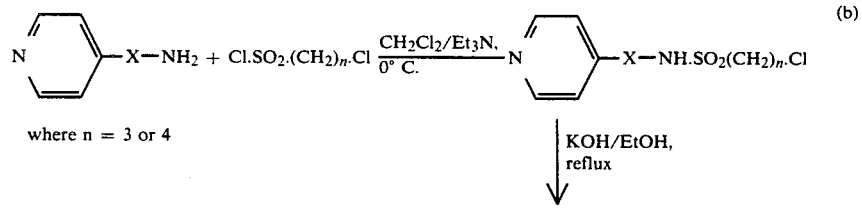
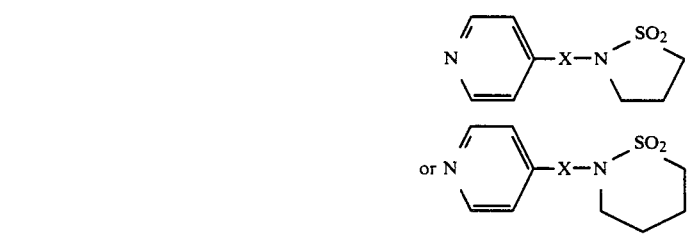
(c)
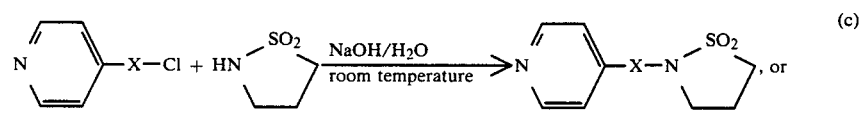
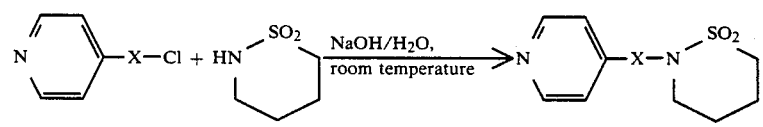
(d)
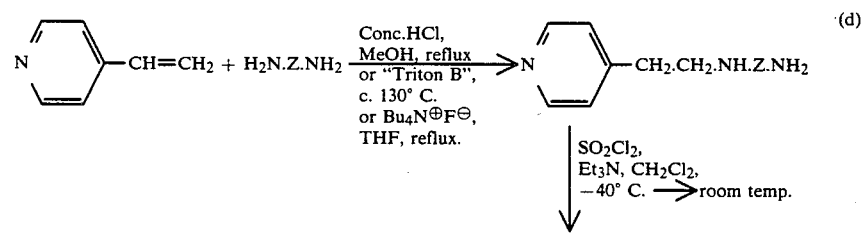
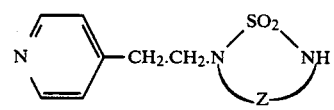
$Z = -CH(R^2)-CH(R^3)-$ or $-CH(R^2)-CH_2-CH(R^3)-$.
As in (a), the vinyl group may be appropriately substituted.
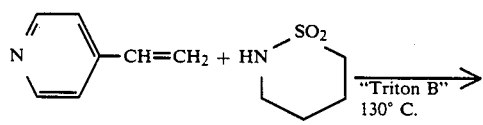

(e)
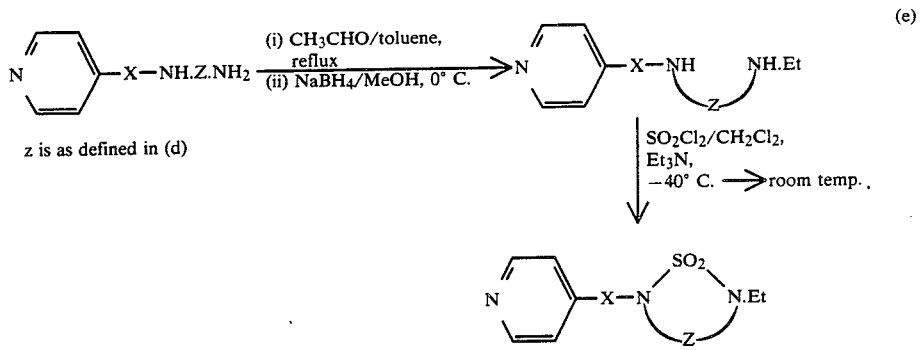
z is as defined in (d)
For the starting material for this route see part (f) next.
Similarly other aldehydes and ketones can be used to obtain compounds having other values for $R^1$.
(f)
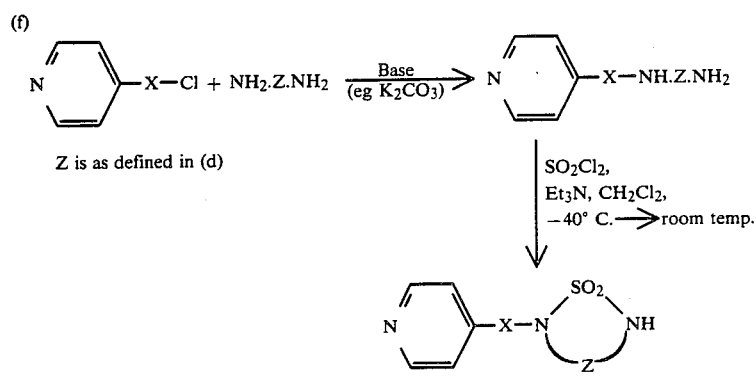
Z is as defined in (d)
(g)
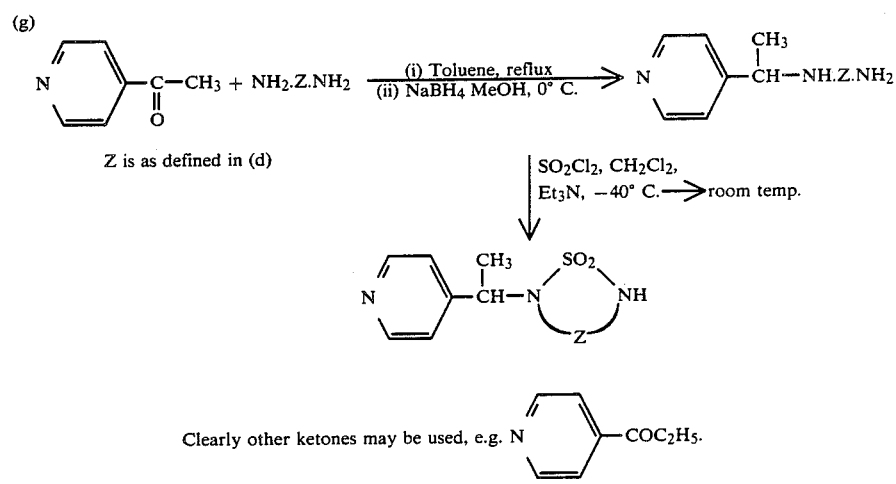
Z is as defined in (d)
Clearly other ketones may be used, e.g. 
(h)
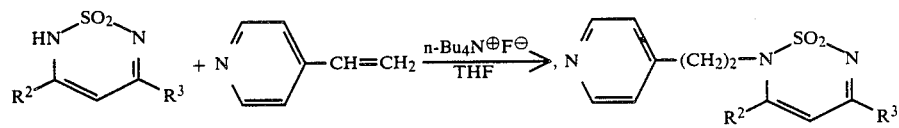
Again the vinyl group can be substituted by $CH_3$ or $C_2H_5$.

-continued (i) 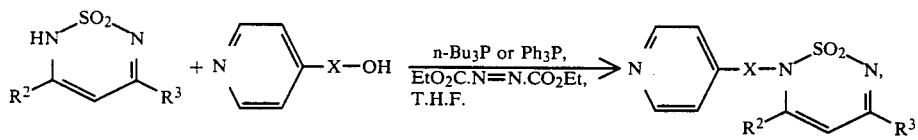

and (j) 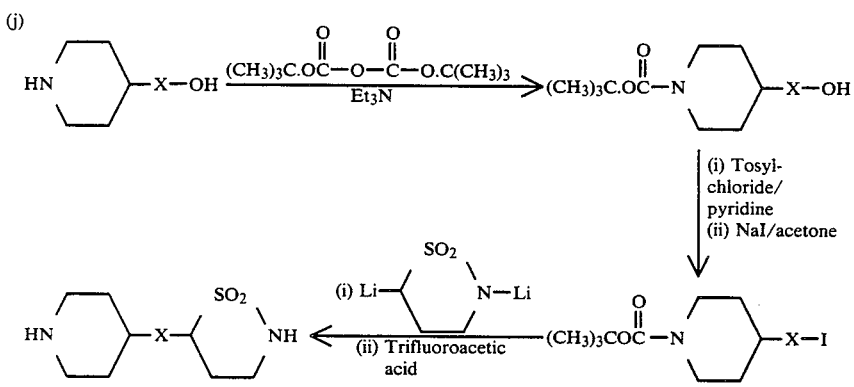

Route B

This route can be illustrated in general terms as follows:

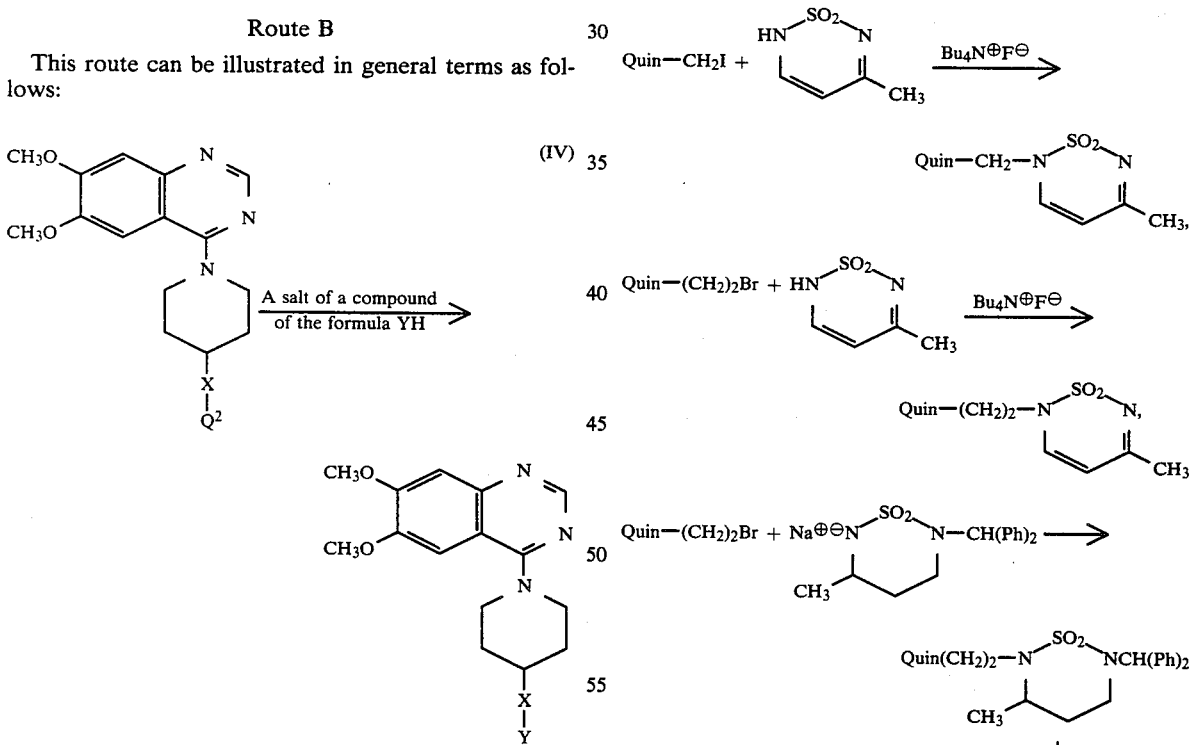

(X and Y are as defined for formula [I])

$Q^2$ is a facile leaving group, e.g., Cl, Br, I or -O.Tosyl. Preferably said salt has the formula $M^{\oplus} Y^{\ominus}$ where M is Na, K, Li or n-Bu$_4$N.

Thus it will be seen that this reaction essentially involves the displacement of a facile leaving group by the anion $Y^{\ominus}$.

Typical reactions, where "Quin"=6,7-dimethoxy-4-piperidinoquinazoline substituted in the 4-position by the stated group, can be represented as follows:

-continued

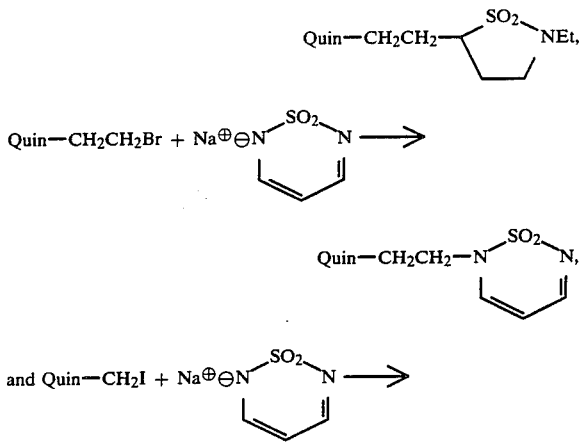

To obtain compounds in which $R^1$ is H it is sometimes necessary to use an N-protected starting material followed by removal of the protecting group after reaction. A preferred protecting group is benzhydryl, removable by $H_2$/Pd.

Typically the reactions are carried out at room temperature in a suitable organic solvent, although heating may sometimes be necessary, e.g. to 80° C., to accelerate the reactions, which are generally complete in 24 hours or less. The products can then be isolated and purified by conventional procedures.

The starting materials are either known compounds or are obtainable conventionally. The lithium salts can for example be obtained by reacting the appropriate heterocycle with lithium diisopropylamide, itself prepared from diisopropylamine and n-butyl lithium. The reaction is typically carried out in tetrahydrofuran at −70° C. under nitrogen. The sodium salts are similarly prepared by reaction with sodium hydride. Again the quinazoline starting materials are preparable conventionally, e.g. as follows:

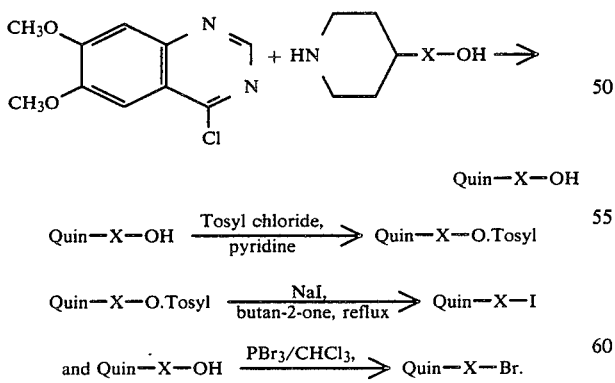

Route C

Compounds of the formula (I) in which $R^1$ is $C_1$–$C_4$ alkyl can also be prepared by the alkylation of the corresponding compounds of the formula (I) in which $R^1$ is H, e.g. by reacting them with a base, e.g. NaH, so as to form the appropriate anion, which anion is then reacted with an alkyl halide of the formula ($C_1$–$C_4$ alkyl).Hal where Hal is Cl, Br or I.

Preferably "Hal" is I.

Thus in a typical reaction a solution of the appropriate quinazoline having $R^1$ as H in a suitable organic solvent, e.g. dimethylformamide, is stirred with sodium hydride for one hour. The alkyl halide is then added and the resulting mixture is stirred at room temperature for up to about 8 hours. If necessary, the reaction mixture can be heated to accelerate the reaction. The product can again be isolated and purified by conventional methods.

Route D

This route can be illustrated as follows:

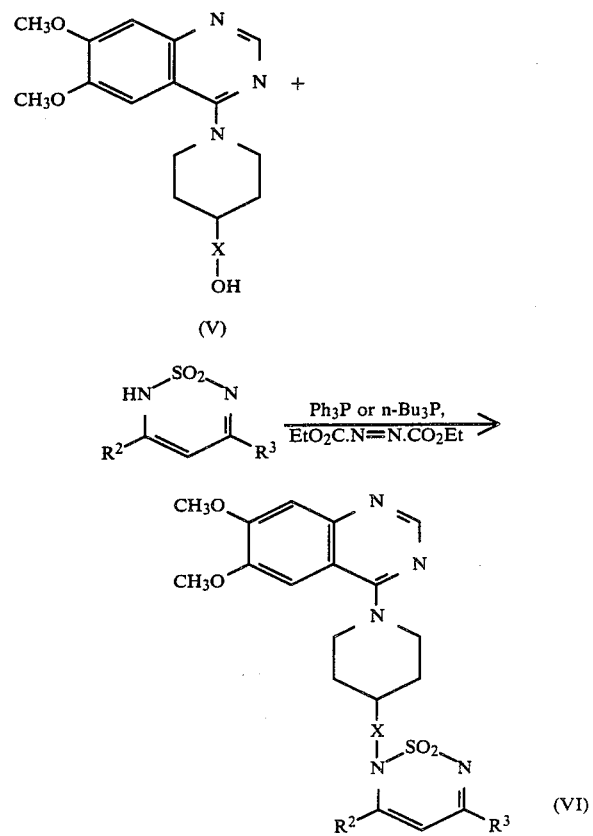

$R^2$, $R^3$ and X are as defined for formula (I).

The reaction can be carried out in a suitable organic solvent, e.g. T.H.F., at room temperature. If necessary, heating at up to reflux temperature can be used to accelerate the reaction.

Route E

The compounds of the formula (I) in which Y is

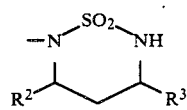

can be prepared by the selective reduction of the corresponding compounds in which Y is

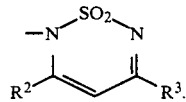

The reduction is typically carried out using sodium borohydride in ethanol at room temperature.

Where the compounds of the invention contain one or more asymmetric centres, then the invention includes the separated enantiomers and diastereoisomers or mixtures thereof. The separated forms can be obtained by conventional means.

The following Examples illustrate the invention (all temperatures in °C.):

EXAMPLE 1

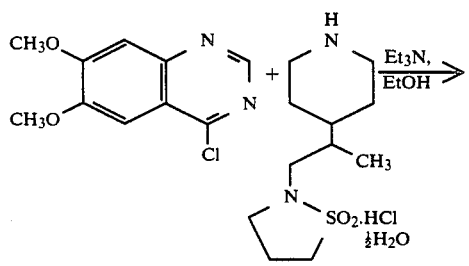

4-Chloro-6,7-dimethoxyquinazoline (0.71 g), 2-[2-(4-piperidyl)prop-1-yl] isothiazolidine-1,1-dioxide hydrochloride hemihydrate (1.00 g) and triethylamine (2.2 cm$^3$) were heated together under reflux for 2.5 hours in ethanol (10 cm$^3$).

The mixture was cooled and volatile material removed in vacuo. The residue was taken into water (25 cm$^3$) and extracted with chloroform (3×25 cm$^3$). The dried (MgSO$_4$) extracts were evaporated in vacuo and the residue was chromatographed on silica (Merck 60.9385) eluting with methanol: ethyl acetate, 1:9, giving an oily residue. This was dissolved in a small quantity of warm ethyl acetate and cyclohexane was added until a faint turbidity was visible. Cooling in the refrigerator afforded 6,7-dimethoxy-4-{4-(1-[1,1-dioxoisothiazolidin-2-yl]prop-2-yl)piperidino} quinazoline, m.p. 129°-131° C.

Analysis %:

Found: C,58.1; H,6.9; N,12.8. Calculated C$_{21}$H$_{30}$N$_4$O$_4$S: C,58.0; H,7.0; N,12.9.

EXAMPLES 2-22

The following compounds were prepared similarly to Example 1, starting from 4-chloro-6,7-dimethoxyquinazoline, triethylamine and the appropriate piperidine (either as the free base or hydrochloride or acetate salt, according to the form in which these piperidines were prepared—see Preparation 10. In cases where a salt of the piperidine is used, excess Et$_3$N should be employed).

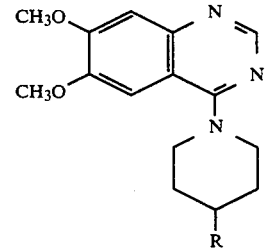

| Example No. | R | Form isolated and m.p. (°C.) | Analysis % (Theoretical in brackets) | | |
|---|---|---|---|---|---|
| | | | C | H | N |
| 2 | —CH$_2$—N(SO$_2$)⌐ (4-membered) | 0.25 H$_2$O, 138° | 55.5 (55.5 | 6.5 6.5 | 13.6 13.6) |
| 3 | —CH$_2$—N(SO$_2$)⌐ (5-membered) | Free base, 155° | 57.4 (57.1 | 7.0 6.7 | 12.7 13.3) |
| 4 | —CH$_2$CH$_2$—N(SO$_2$)⌐ (4-membered) | Free base, 192-193° | 56.8 (57.1 | 6.8 6.7 | 13.0 13.3) |
| 5 | —CH$_2$CH$_2$—N(SO$_2$)⌐ (5-membered) | Free base, 159° | 57.8 (58.0 | 7.0 7.0 | 12.6 12.9) |

-continued

| Example No. | R | Form isolated and m.p. (°C.) | Analysis % (Theoretical in brackets) C | H | N |
|---|---|---|---|---|---|
| 6 | -CH(CH₃)-CH₂-N(SO₂)(CH₂)₄ (piperidine sulfonyl, 6-ring) | Free base, 156° | 58.6 (58.9 | 7.2 7.2 | 12.5 12.5) |
| 7 | -CH(CH₃)-N(SO₂)(CH₂)₃ (5-ring) | Free base, 185–187° | 57.1 (57.1 | 6.7 6.7 | 13.1 13.3) |
| 8 | -CH₂-N(SO₂)NH (5-ring) | Free base, 193–195° | 53.2 (53.1 | 6.2 6.2 | 17.1 17.2) |
| 9 | -CH₂-N(SO₂)NH (6-ring) | Solvate with 0.5 mole ethyl acetate, 131–133° | 54.5 (54.2 | 6.6 6.7 | 15.0 15.0) |
| 10 | -CH₂CH₂-N(SO₂)NH (5-ring) | Monohydrate, 179° | 54.6 (54.1 | 6.5 6.5 | 16.6 16.6) |
| 11 | -CH₂CH₂-N(SO₂)NH (6-ring) | Free base, 130° | 54.9 (55.1 | 6.6 6.7 | 16.3 16.1) |
| 12 | -CH₂CH₂-N(SO₂)NEt (6-ring) | monohydrate, 135° | 54.7 (54.9 | 7.0 7.3 | 14.3 14.5) |
| 13 | -CH(CH₃)-N(SO₂)NH (5-ring) | Free base, 186–188° | 54.3 (54.1 | 6.6 6.5 | 16.8 16.6) |
| 14 | -CH(CH₃)-N(SO₂)NH (6-ring) | Free base, 197–199° | 55.1 (55.1 | 6.8 6.7 | 15.8 16.1) |
| 15 | -CH(CH₃)CH₂-N(SO₂)NH (5-ring) | Free base, 180° | 55.4 (55.2 | 6.6 6.7 | 15.9 16.1) |
| 16 | -CH(CH₃)CH₂-N(SO₂)NH (6-ring) | Free base, 162–163° | 55.9 (56.1 | 6.9 6.9 | 15.9 15.6) |
| 17 | -CH(C₂H₅)-N(SO₂)NH (6-ring) | Free base, 210–211° | 55.8 (56.1 | 6.7 6.9 | 15.7 15.6) |
| 18* | -CH₂-CH₂-N(SO₂)NH (6-ring, with CH₃ substituent) | Free base, 183–185° | 55.0 (55.1 | 6.8 6.7 | 16.1 16.1) |

| Example No. | R | Form isolated and m.p. (°C.) | Analysis % (Theoretical in brackets) C H N |
|---|---|---|---|
| 19* | —CH₂CH₂—N(SO₂NH)CH₃ (6-membered, methyl substituent) | Free base, 169–172° | 54.9 6.8 16.0 (55.1 6.7 16.1) |
| 20 | —CH₂—N(SO₂NH)CH₃ | Free base, 220–221° | 54.9 6.8 16.1 (55.1 6.7 16.1) |
| 21 | —CH₂CH₂—N(SO₂NH)CH₃ | Free base, 182–184° | 55.9 6.8 15.5 (56.1 6.9 15.6) |
| 22 | —CH(CH₃)CH₂—N(SO₂NH)CH₃ | Free base, 90–93° | 56.0 7.0 15.1 (56.1 7.0 15.6) |

*These compounds were prepared by reaction of 4-chloro-6,7-dimethoxyquinazoline, triethylamine and the 3:1 mixture (as hydrochlorides) of 2-[2-(4-piperidyl)ethyl]-4-methyl-1,2,5-thiadiazolidine-1,1-dioxide and 2-[2-(4-piperidyl)ethyl]-3-methyl-1,2,5-thiadiazolidine-1,1-dioxide, chromatography on silica separating the mixture of products into the compounds of Example 18 and 19.

EXAMPLE 23

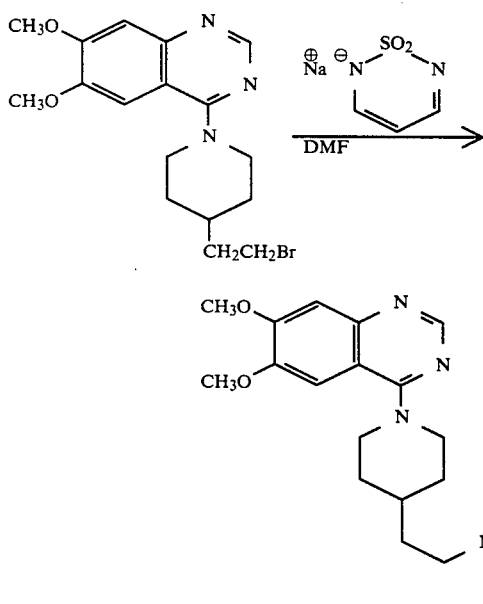

Sodium hydride (0.19 g. of a 50% dispersion in oil) was added to a stirred solution of 2H-1,2,6-thiadiazine-1,1-dioxide (0.52 g) in dimethylformamide (4 cm³). After 0.5 hours 1-(6,7-dimethoxyquinazolin-4-yl)-4-(2-bromoethyl)piperidine (0.60 g) was added and the mixture was warmed at 70° for 10 hours. The solvent was removed in vacuo, water was added and the mixture was extracted with chloroform (4×20 cm³). The dried (MgSO₄) extracts were evaporated and the residue was chromatographed on silica (Merck 60. 9385) eluting with methanol:ethyl acetate, 1:19, to give an oil which was crystallised from ethyl acetate to afford 1-(6,7-dimethoxyquinazolin-4-yl)-4-[2-(1,1-dioxo-1,2,6-thiadiazin-2-yl)ethyl]piperidine as microcrystals, m.p. 176°–8°, (0.18 g).

Analysis %: Found: C,55.8; H,6.0; N,16.5. Calculated for C₂₀H₂₅N₅O₄S: C,55.7; H,5.8; N,16.2.

The following compounds were prepared similarly to the previous Example, starting from 1-(6,7-dimethoxyquinazolin-4-yl)-4-(2-bromoethyl)piperidine and the appropriate sodio-derivative of the heterocycle.

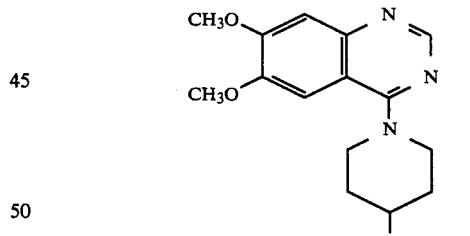

| Example No. | R | Form isolated and m.p. (°C.) | Analysis % (Theoretical in brackets) C H N |
|---|---|---|---|
| 24 | —N(SO₂N)=C(CH₃)—CH=C(CH₃)— | Monohydrate, 134–138° | 55.7 6.4 14.5 (53.3 6.5 14.7) |
| 25 | —N(SO₂NH)CH(CH₃)CH₂CH(CH₃) | Free base, 110–112° | 56.8 7.6 14.6 (57.0 7.2 15.1) |

EXAMPLE 26

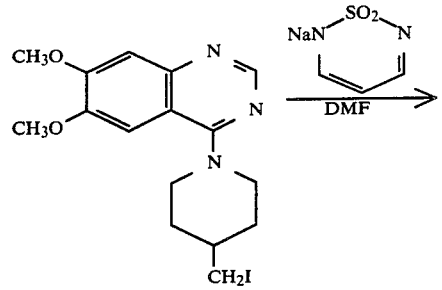

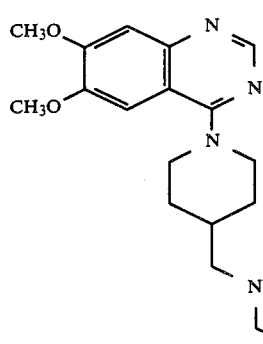

| Example No. | R | Form isolated and m.p. (°C.) | Analysis % (Theoretical in brackets) | | |
|---|---|---|---|---|---|
| | | | C | H | M |
| 27 | −CH$_2$−N(SO$_2$)N=C(CH$_3$)−CH=C(CH$_3$) | 0.5 H$_2$O, 198−200° | (55.5 | 6.0 6.2 | 15.3 15.4) |
| 28 | −CH$_2$−N(SO$_2$)NH, CH(CH$_3$)CH$_2$CH(CH$_3$) | 0.5 H$_2$O, 210−212° | 54.8 (55.0 | 6.9 7.0 | 15.4 15.3) |
| 29 | −(CH$_2$)$_3$−N(SO$_2$) | 1 H$_2$O, 142−143° | 55.8 (55.7 | 6.8 7.1 | 12.3 12.4) |

EXAMPLE 30

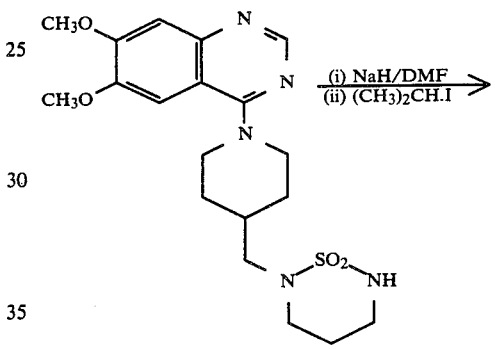

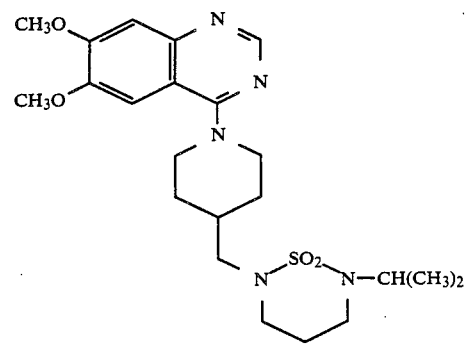

Sodium hydride (0.20 g. of a 50% dispersion in oil) was added to a stirred solution of 2H-1,2,6-thiadiazine-1,1-dioxide (0.56 g) in dimethylformamide (4 cm$^3$). After 0.5 hours 1-(6,7-dimethoxyquinazolin-4-yl)-4-iodomethylpiperidine (0.70 g) was added and the mixture was warmed at 70° for 10 hours. The solvent was removed in vacuo, water was added and the mixture was extracted with chloroform (4×20 cm$^3$). The dried (MgSO$_4$) extracts were evaporated and the residue was chromatographed on silica (MK 60.9385) eluting with methanol:ethyl acetate, 1:19, to give a foam. Crystallisation from ethyl acetate afforded 1-(6,7-dimethoxyquinazolin-4-yl)-4-(1,1-dioxo-1,2,6-thiadiazin-2-yl)methyl piperidine as white microcrystals, m.p. 173°−174°, (0.27 g).

Analysis %: Found: C,54.9; H,5.5; N,16.7. Calculated for C$_{19}$H$_{23}$N$_5$O$_4$S: C,54.7; H,5.5; N,16.8.

The following compounds were prepared similarly to the previous Example starting from 1-(6,7-dimethoxyquinazolin-4-yl)-4-iodomethylpiperidine or 1-(6,7-dimethoxyquinazolin-4-yl)-4-(3-iodoprop-1-yl)piperidine and the appropriate sodio-derivative of the heterocycle.

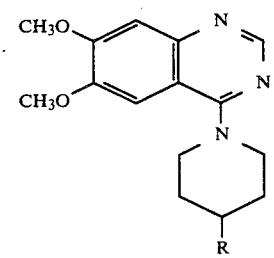

A stirred solution of 1-(6,7-dimethoxyquinazolin-4-yl)-4-[(1,1-dioxotetrahydro-1,2,6-thiadiazin-2-yl)methyl]piperidine ½ CH$_3$CH$_2$OCOCH$_3$ (0.7 g) (prepared as in Example 9) in dimethylformamide (4.0 cm$^3$) was treated at room temperature with sodium hydride (100 mg. of a 50% dispersion in oil) and the mixture was stirred for 45 minutes. Isopropyl iodide (255 mg) was then added and the resulting mixture was stirred for 6 hours. The solvent was removed in vacuo and the residue was taken into chloroform (50 cm$^3$) and water (25 cm$^3$). The aqueous phase was extracted with chloroform (2×20 cm$^3$) and the dried (MgSO$_4$) extracts were evaporated to yield an oil which was chromatographed on silica (Merck 60.9385) eluting with chloroform to give a gum. Crystallisation from ethyl acetate afforded 1-(6,7-dimethoxyquinazolin-4-yl)-4-([1,1-dioxo-6-isopropyltetrahydro-1,2,6-thiadiazin-2-yl]methyl)piperidine, m.p. 158°–161° (460 mg).

Analysis %: Found: C,56.7; H,7.2; N,15.3. Calculated for $C_{22}H_{33}N_5O_4S$: C,57.0; H,7.2; N,15.1%.

EXAMPLE 31

The following compound, m.p. 147°–149°, was prepared similarly to the previous example, starting from the sodium salt of 1-(6,7-dimethoxyquinazolin-4-yl)-4-[(1,1-dioxotetrahydro-1,2,6-thiadiazin-2-yl)methyl]-piperidine. ½ $CH_3CH_2OCOCH_3$ and $CH_3I$:

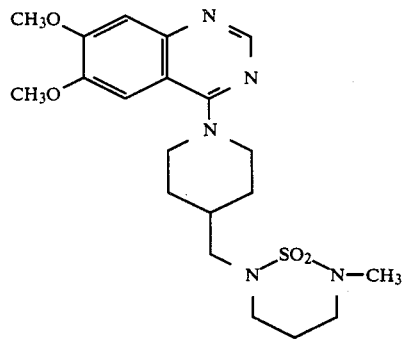

Analysis %: Found: C,55.1; H,6.7; N,16.0; Calculated for $C_{20}H_{29}N_5O_4S$: C,55.1; H,6.7; N,16.1.

EXAMPLE 32

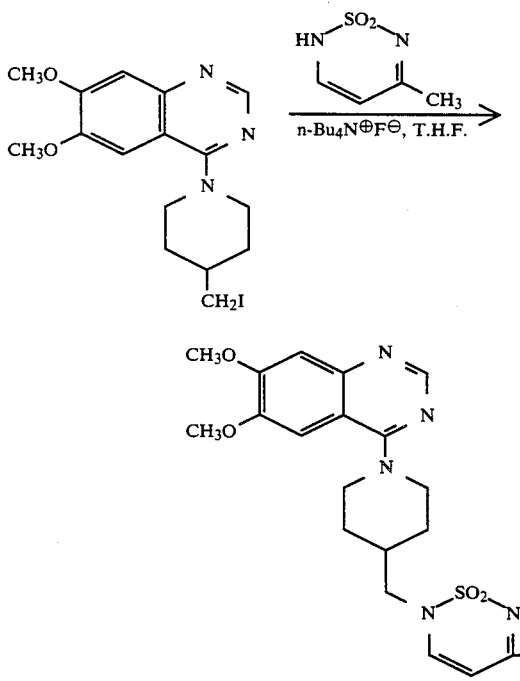

A mixture of 3-methyl-6H-1,2,6-thiadiazine-1,1-dioxide (0.584 g) and 1-(6,7-dimethoxyquinazolin-4-yl)-4-iodomethylpiperidine (0.826 g) were heated under reflux with tetrabutylammonium fluoride (4 ml; 1.0M in tetrahydrofuran [T.H.F.]) for 24 hours. The solvent was then removed in vacuo and the residue was chromatographed on silica (Merck 60.9385) eluting with chloroform to give a foam. Crystallisation from ethyl acetate gave 1-(6,7-dimethoxyquinazolin-4-yl)-4-(1,1-dioxo-5-methyl-1,2,6-thiadiazin-2-yl)methylpiperidine as white needles, m.p. 203°–207°, (0.35 g).

Analysis %: Found: C,55.6; H,5.9; N,16.1. Calculated for $C_{20}H_{25}N_5O_4S$: C,55.7; H,5.8; N,16.2.

The following compound was prepared similarly to the previous example, starting from 1-(6,7-dimethoxyquinazolin-4-yl)-4-(2-bromoethyl)piperidine, tetrabutylammonium fluoride and the appropriate heterocycle.

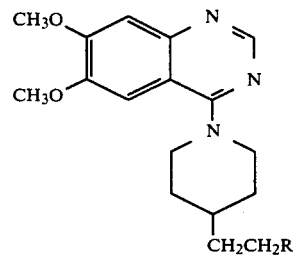

| Example No. | R | Form Isolated and m.p. (°C.) | Analysis % (Theoretical in brackets) | | |
|---|---|---|---|---|---|
| | | | C | H | N |
| 33 | —N(SO₂)N=CH—CH₃ | Free base, 142–145° | 56.7 (56.6 | 6.3 6.1 | 15.6 15.7) |

The following compounds were prepared similarly to Example 32 starting from 1-(6,7-dimethoxyquinazolin-4-yl)-4-(1-bromo-prop-2-yl)piperidine, tetrabutylammonium fluoride and the appropriate heterocycle.

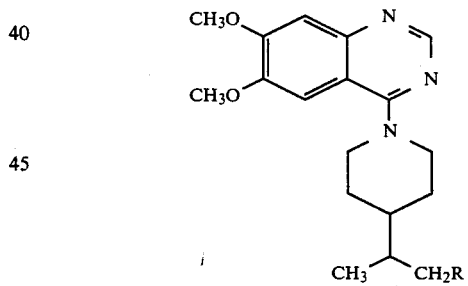

| Example No. | R | Form Isolated and m.p. (°C.) | Analysis % (Theoretical in brackets) | | |
|---|---|---|---|---|---|
| | | | C | H | N |
| 34 | —N(SO₂)N= | Free base, 175–177° | 56.6 (56.6 | 6.2 6.1 | 15.6 15.7) |
| 35 | —N(SO₂)N=CH—CH₃ | Free base, 174–176° | 57.2 (57.5 | 6.5 6.4 | 15.0 15.2) |

The following compounds were prepared similarly to Example 32 starting from 1-(6,7-dimethoxyquinazolin- 4-yl)-4-(3-iodo-prop-1-yl)piperidine, tetrabutylammonium fluoride and the appropriate heterocycle.

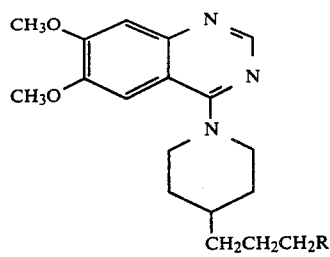

| Example No. | R | Form Isolated and m.p. (°C.) | Analysis % (Theoretical in brackets) | | |
|---|---|---|---|---|---|
| | | | C | H | N |
| 36 | —N(SO₂)N (ring) | Hydrochloride, 105–106° | 52.0 (52.3 | 5.9 5.9 | 14.0 14.5) |
| 37 | —N(SO₂)N-CH₃ (ring) | Free base, | 57.3 (57.5 | 6.4 6.4 | 14.9 15.3) |

The following compounds were prepared similarly to Example 32 starting from 1-(6,7-dimethoxyquinazolin-4-yl)-4-(1-iodo-but-3-yl)piperidine, tetrabutylammonium fluoride and the appropriate heterocycle.

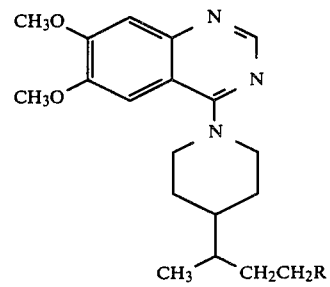

| Example No. | R | Form Isolated and m.p. (°C.) | Analysis % (Theoretical in brackets) | | |
|---|---|---|---|---|---|
| | | | C | H | N |
| 38 | —N(SO₂)N (ring) | Monohydrochloride 1.5 H₂O, 170–173° | 50.2 (50.5 | 6.0 6.4 | 13.4 13.4) |
| 39 | —N(SO₂)N-CH₃ (ring) | Free base, 126–128° | 58.2 (58.3 | 6.6 6.6 | 14.6 14.8) |

EXAMPLE 40

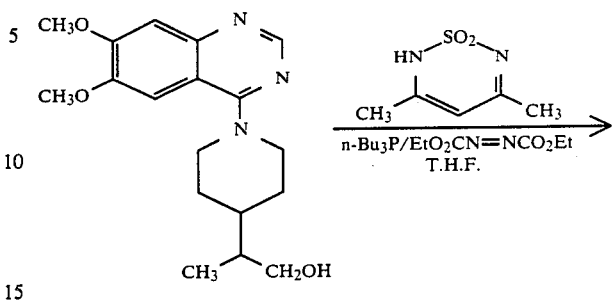

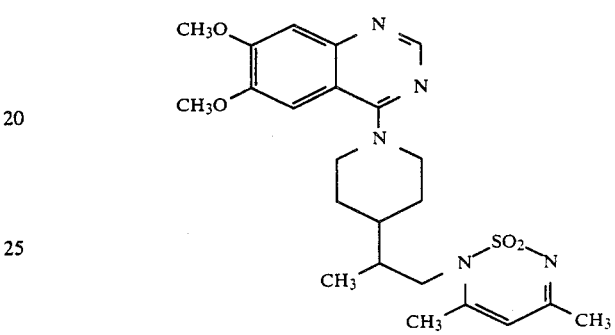

A mixture of 1-(6,7-dimethoxyquinazolin-4-yl)-4-(1-hydroxy-prop-2-yl)piperidine (0.99 g), tri-n-butylphosphine (1.5 ml) and 2H-3,5-dimethyl-1,2,6-thiadiazine-1,1-dioxide (0.96 g) in T.H.F. (30 ml) were treated at room temperature with diethylazodicarboxylate (0.94 ml). After stirring for 24 hours, the solvents were removed in vacuo and the residue was chromatographed on silica (Merck 60.9385) eluting with chloroform:methanol (50:1) to give a foam. Crystallisation from methanol-ethyl acetate afforded 1-(6,7-dimethoxyquinazolin-4-yl)-4-[1-(1,1-dioxo-3,5-dimethyl-1,2,6-thiadiazin-2-yl)prop-2-yl]piperidine as white microcrystals, m.p. 169°–172°, (0.338 g).

Analysis %: Found: C,58.4; H,6.8; N,14.5. Calculated for $C_{23}H_{31}N_5O_4S$: C,58.3; H,6.6; N,14.8.

The following compound was prepared similarly to the previous example starting from 1-(6,7-dimethoxyquinazolin-4-yl)-4-(2-hydroxyprop-1-yl)piperidine, triphenylphosphine, diethylazodicarboxylate and the appropriate heterocycle, and warming at 50° for 24 hours.

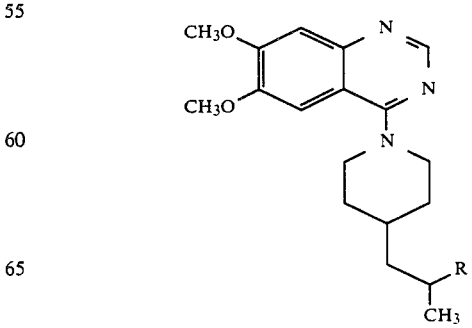

| Example No. | R | Form Isolated and m.p. (°C.) | Analysis % (Theoretical in brackets) | | |
|---|---|---|---|---|---|
| | | | C | H | N |
| 41 | 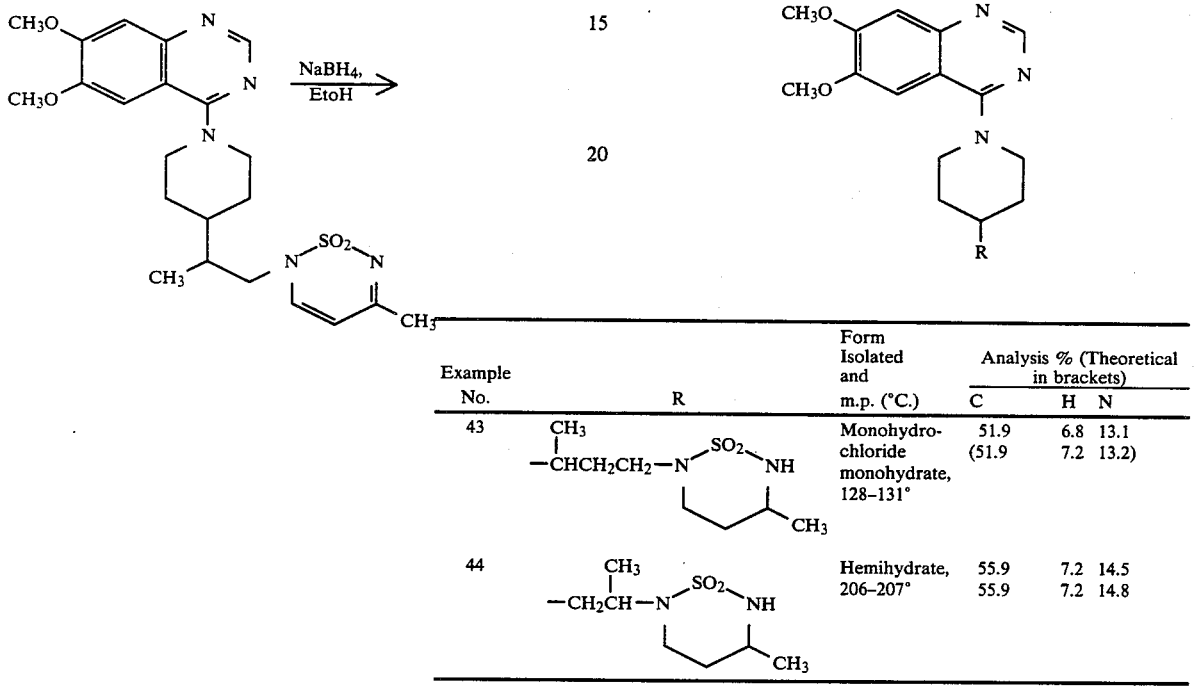 | Free base, 158–160° | 57.5 (57.5 | 6.5 6.4 | 15.2 15.2) |

EXAMPLE 42

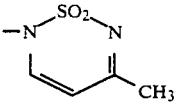

Sodium borohydride (0.025 g) was added at room temperature to a stirred solution of 1-(6,7-dimethoxyquinazolin-4-yl)-4-[1-(1,1-dioxo-5-methyl-1,2,6-thiadiazin-2-yl)prop-2-yl]piperidine (0.30 g) (Example 35) in absolute ethanol (5 ml.). After stirring for 16 hours, the mixture was acidified to pH1 with 2M hydrochloric acid and concentrated in vacuo. The residue was treated with aqueous sodium carbonate solution to pH12, extracted with chloroform (3×10 ml.), and the combined extracts were dried (MgSO₄) and evaporated to yield an oil which was chromatographed on silica ("Merck 60.9385") eluting with methanol:ethyl acetate, 1:20, to give a solid. Recrystallisation from ethyl acetate-ether afforded 1-(6,7-dimethoxyquinazolin-4-yl)-4-[1-(1,1-dioxo-5-methyltetrahydro-1,2,6-thiadiazin-2-yl)prop-2-yl]piperidine as white microcrystals, m.p. 172°–175°, (0.15 g).

Analysis %: Found: C,57.2; H,7.3; N,14.6. Calculated for C₂₂H₃₃N₅O₄S: C,57.0; H,7.2; N,15.1.

The following compounds were prepared similarly to the previous example using sodium borohydride and the products of, respectively, examples 39 and 41, as starting materials.

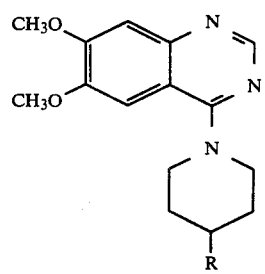

| Example No. | R | Form Isolated and m.p. (°C.) | Analysis % (Theoretical in brackets) | | |
|---|---|---|---|---|---|
| | | | C | H | N |
| 43 | 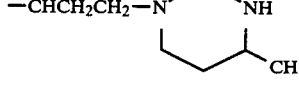 | Monohydrochloride monohydrate, 128–131° | 51.9 (51.9 | 6.8 7.2 | 13.1 13.2) |
| 44 | 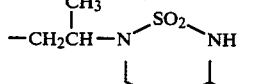 | Hemihydrate, 206–207° | 55.9 55.9 | 7.2 7.2 | 14.5 14.8 |

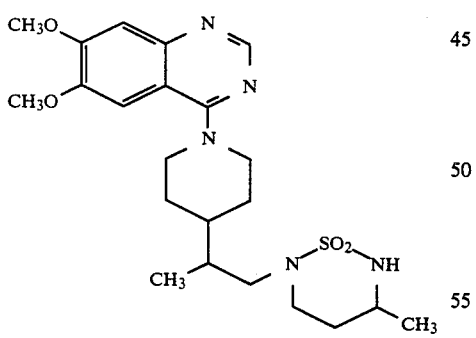

EXAMPLE 45

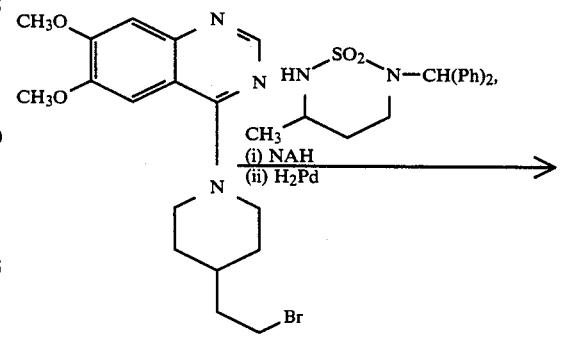

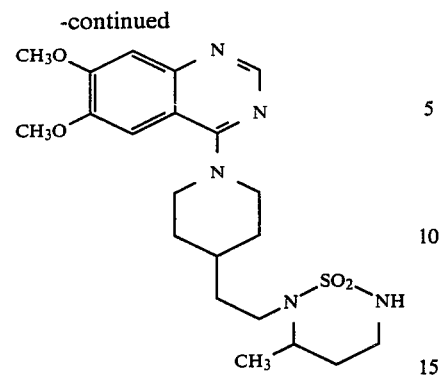

Sodium borohydride (0.12 g) was added at room temperature to a stirred suspension of 1,1-dioxo-2-benzhydryl-5-methyl-1,2,6-thiadiazine (1.00 g) and the mixture was stirred for 16 hours. The mixture was then acidified carefully to pH6 with glacial acetic acid and concentrated in vacuo. After treatment with aqueous sodium carbonate solution, the mixture was extracted with chloroform (5×25 ml) and the combined extracts were dried (MgSO$_4$) and evaporated to give a white solid (1.06 g). This solid was a mixture of the partially and fully reduced thiadiazine in a ratio of 1:4 by n.m.r.

This material was taken without purification into dry D.M.F. (12 ml) and treated with sodum hydride (0.18 g of a 50% dispersion in oil) and stirred for ½ hour, after which time 1-(6,7-dimethoxyquinazolin-4-yl)-4-(2-bromoethyl)piperidine (1.27 g) was added and the mixture was heated at 60° for 16 hours. Volatile material was then removed in vacuo and the product was isolated by chromatography on silica ("Merck 60.9385") eluting with methanol:chloroform, 1:50, to give an oil (1.40 g). A portion of this material (1.24 g) was hydrogenated over palladised charcoal (120 mg., 10%) at 60° and 60 p.s.i. pressure until hydrogen uptake ceased. The mixture was filtered through "Solkafloc" (Trade Mark), concentrated in vacuo, and chromatographed on silica ("Merck 60.9385") eluting with chloroform:methanol, 50:1, to afford the product as an oil which crystallised on treatment with ethereal hydrogen chloride to give 1-(6,7-dimethoxyquinazolin-4-yl)-4-[2-(1,1-dioxo-3-methyltetrahydro-1,2,6-thiadiazin-2-yl)ethyl]piperidine monohydrochloride, m.p. 196°–199°, (0.087 g).

Analysis %: Found: C,51.6; H,6.6; N,14.3 Calculated for C$_{21}$H$_{32}$N$_5$O$_4$SCl: C,51.9; H,6.6; N,14.4.

EXAMPLE 46

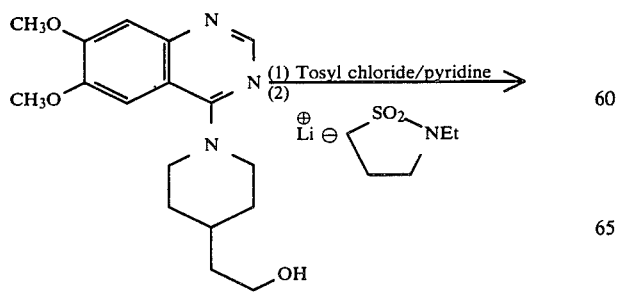

Toluene-4-sulphonylchloride (1.14 g) was added to a stirred solution of 1-(6,7-dimethoxyquinazolin-4-yl)-4-(2-hydroxyethyl) piperidine (1.71 g) in pyridine (15 cm$^3$) at 0° C. After stirring for 16 hours at room temperature water (25 cm$^3$) was added and the solution was extracted with chloroform (3×50 cm$^3$). The dried (MgSO$_4$) extracts were evaporated in vacuo and the residue was chromatographed on silica ("Merck 60.9385") eluting with methanol:ethyl acetate, 1:19, to give the tosylate, m.p. 143°–147° (2.3 g). A portion (1.0 g) of this material was taken without further purification into tetrahydrofuran (25 cm$^3$) at 0° C. under nitrogen and treated with a solution of 5-lithio-2-ethylisothiazolidine-1,1-dioxide (0.31 g) [prepared from 2-ethylisothiazolidine-1,1-dioxide and n-butyl lithium] in tetrahydrofuran (15 cm$^3$). The mixture was allowed to warm to room temperature over 1 hours and water (10 cm$^3$) was added. The mixture was evaporated in vacuo and water (20 cm$^3$) and chloroform (50 cm$^3$) were added. The organic phase was further extracted with chloroform (2×40 cm$^3$) and the dried (MgSO$_4$) extracts were evaporated to give a white solid. Crystallisation from ethyl acetate afforded 1-(6,7-dimethoxyquinazolin-4-yl)-4-[2-(2-ethyl-1,1-dioxoisothiazolidin-5-yl)ethyl]piperidine as white crystals, m.p. 130°, (0.30 g).

Analysis %: Found: C,58.9; H,7.1; N,12.5. Calculated for C$_{22}$H$_{32}$N$_4$O$_4$S: C,59.2; H,6.8; N,12.0.

EXAMPLE 47

The following compound, m.p. 204°–206°, was prepared similarly to Example 1, starting from 4-chloro-6,7-dimethoxyquinazoline, 5-(2-[4-piperidyl]ethyl)isothiazolidine-1,1-dioxide, and triethylamine.

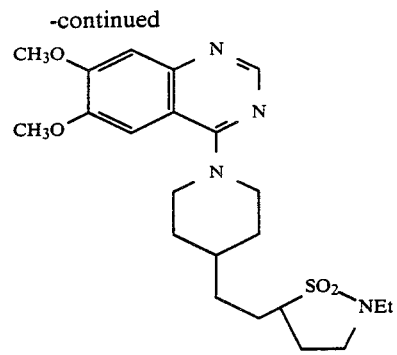

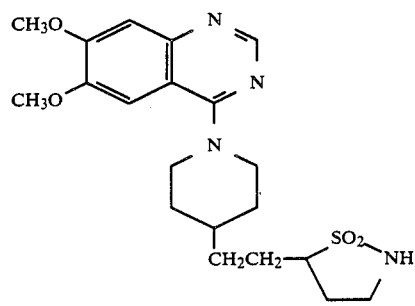

Analysis %: Found: C,56.8; H,6.7; N,13.2; Calculated for C$_{20}$H$_{28}$N$_4$O$_4$S: C,57.1; H,6.7; N,13.3.

EXAMPLE 48

Preparation of certain acid addition salts of 4-[4-{2-(1,1-dioxo-2-isothiazolidinyl)ethyl}piperidino]-6,7-dimethoxyquinazoline (product of Example 4)

(a) Hydrochloride salt

Concentrated hydrochloric acid (20.2 ml) was added over 5 minutes to a suspension of 4-[4-{2-(1,1-dioxo-2-isothiazolidinyl)ethyl}piperidino]-6,7-dimethoxyquinazoline (100 g) in industrial methylated spirits (1 liter). The mixture was heated to 45° and then cooled and stirred at 0° for 1 hour. The hydrochloride salt was filtered and dried in vacuum giving 105.5 g of the salt having m.p. 227°–229°.

Analysis %: Found: C,52.75; H,6.45; N,12.15. Calculated for $C_{20}H_{28}N_4O_4S.HCl$: C,52.56; H,6.4; N,12.26.

(b) Tosylate salt

A solution of p-toluenesulphonic acid (4.5 g) in acetone (20 ml) was added to a suspension of 4-[4-{2-(1,1-dioxo-2-isothiazolidinyl)ethyl}piperidino]-6,7-dimethoxyquinazoline (10 g.) in acetone (82 ml) at room temperature. Complete solution was obtained after which the product crystallised and was stirred at 0° for 1 hour. The tosylate salt was filtered, washed with acetone and recrystallised from acetone/industrial methylated spirit to give 9.7 g of the salt having m.p. 156°–7°.

(c) Tartrate salt

A mixture of 4-[4 -{2-(1,1-dioxo-2-isothiazolidinyl)ethyl}piperidino]-6,7-dimethoxyquinazoline (10 g), (+) tartaric acid (3.6 g), industrial methylated spirits (70 ml) and water (10 ml) was heated to reflux to give a clear solution. The mixture was then cooled to 0° and granulated for 1 hour. The tartrate salt was filtered and washed with industrial methylated spirit. Recrystallisation from aqueous industrial methylated spirit gave 11.1 g of the tartrate salt having m.p. 116°–118°.

The following Preparations illustrate the synthesis of certain of the starting materials. All temperatures are in °C.

PREPARATION 1

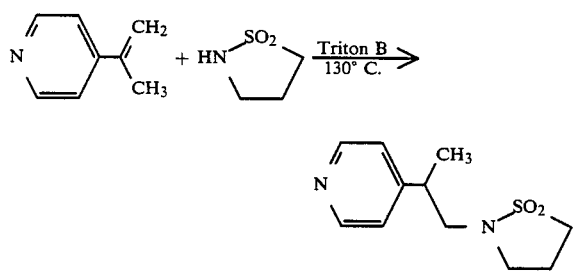

A mixture of 4-isopropenyl pyridine (1.79 g) and isothiazolidine-1,1-dioxide (1.81 g) was heated at 130° C. during the addition of "Triton B" (Trade Mark, trimethylbenzylammonium hydroxide) (0.25 g added every hour for four hours; 40% solution in water). After stirring for 16 hours at 130° the mixture was cooled and taken in chloroform (50 cm³) and water (50 cm³). The aqueous phase was extracted with chloroform (3×20 cm³) and the dried (MgSO₄) extracts were evaporated to given an oil. Chromatography on silica ("Merck 60. 9385") eluting with ethyl acetate gave 2-[2-(4-pyridyl)-prop-1-yl]isothiazolidine-1,1-dioxide which crystallised from ethyl acetate-hexane as needles, m.p. 90°–92° (1.01 g).

Analysis %:
Found: C,55.0; H,6.8; N,12.0. Calculated for $C_{11}H_{16}N_2O_2S$: C,55.0; H,6.7; N,11.7.

Also synthesised by a similar method were:
2-[2-(4-pyridyl)prop-1-yl]-tetrahydro-1,2-thiazine-1,1-dioxide (crude base, oil), and
2-[2-(4-pyridyl)ethyl]-tetrahydro-1,2-thiazine-1,1-dioxide (crude base, m.p. 40°–45°).

PREPARATION 2

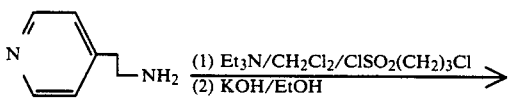

A solution of 3-chloropropanesulphonyl chloride (20.0 g) in dichloromethane (200 cm³) was added dropwise over 1.5 hours to a stirred solution of 4-(2-aminoethyl)pyridine (13.8 g) in dichloromethane (200 cm³) and triethylamine (15 cm³) at 0° C. The ice bath was removed and the mixture was stirred for 16 hours. Saturated aqueous sodium carbonate (100 cm³) was then added and the organic phase was dried (MgSO₄) and evaporated in vacuo to yield an oil which was suspended in abs. ethanol (500 cm³) and heated under reflux with potassium hydroxide (6.3 g) for 0.5 hours. The mixture was cooled and filtered and the filtrate was evaporated in vacuo to yield an oil which was taken into warm ethyl acetate (100 cm³), charcoal was added and the mixture was filtered. The filtrate was passed through a "Florisil" column (Trade Mark, Hopkin and Williams) and eluted further with ethyl acetate to obtain a colourless oil. Crystallisation from ethyl acetate gave 2-[2-(4-pyridyl)ethyl]isothiazolidine-1,1-dioxide as colourless needles, m.p. 70° C. (15.0 g).

Analysis %: Found: C,52.7; H,6.2; N,12.2. Calculated for $C_{10}H_{14}N_2O_2S$: C,53.1; H,6.2; N,12.4.

Also synthesized by a similar method was:
2-[1-(4-pyridyl)ethyl]isothiazolidine-1,1-dioxide (crude base, oil).

PREPARATION 3

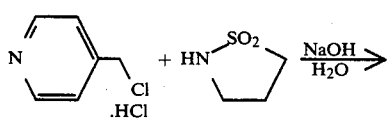

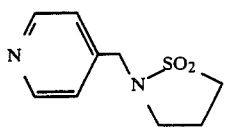

A mixture of 4-picolylchloride hydrochloride (2.7 g) was stirred in water (10 cm³) with sodium hydroxide (1.3 g) during the addition of isothiazolidine-1,1-dioxide (2.0 g) in water (5 cm³). After stirring for 2 hours the mixture was extracted with chloroform (3×15 cm³) and the dried (MgSO₄) extracts were evaporated in vacuo to give an oil which was chromatographed on silica (MK 60. 9385) eluting with ethyl acetate to give an oil which crystallised from ethyl acetate affording 2-(4-pyridylmethyl)isothiazolidine-1,1-dioxide as white crystals, m.p. 82° (3.5 g).

Analysis %: Found: C,50.9; H,5.7; N,13.3. Calculated for $C_9H_{12}N_2O_2S$: C,50.9; H,5.7; N,13.2.

Also synthesised by a similar method was:
2-(4-pyridylmethyl)tetrahydro-1,2-thiazine,1,1-dioxide (crude base, oil).

PREPARATION 4

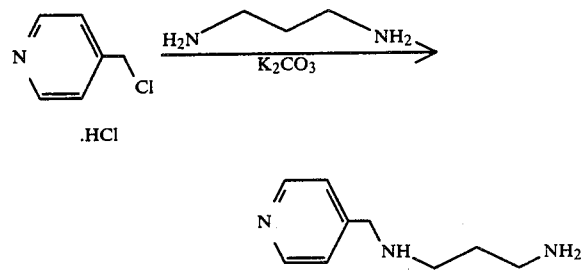

A solution of potassium carbonate (4.3 g) in water (10 cm³) was added to a solution of 4-picolylchloride hydrochloride (10.0 g) in water (10 cm³). The yellow oil which separated was added to the stirred 1,3-diaminopropane (20.0 cm³) and the mixture was heated on a steam bath for 1 hour. After cooling, the excess of 1,3-diaminopropane was removed in vacuo and the residue was taken into absolute alcohol (70 cm³). The solution was treated with potassium hydroxide (3.5 g) and stirred for 45 minutes. The precipitate was filtered off, the filtrate was concentrated in vacuo and the residue was distilled to give N-(4-pyridylmethyl)-1,3-diaminopropane (6.73 g; 67%) as a colourless oil, b.p. 135°/0.3 mm (Kugelrohr).

N-(4-Puridylmethyl)-1,2-diaminoethane is a known compound.

PREPARATION 5

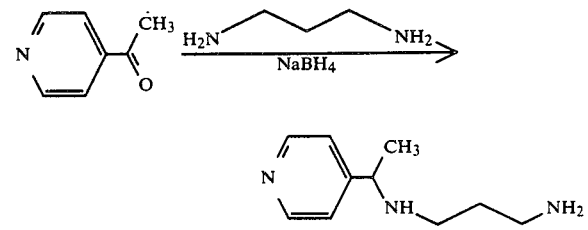

4-Acetylpyridine (30.3 g) was added portionwise over 40 minutes to a solution of 1,3-diaminopropane (85 cm³) in toluene (250 cm³) under reflux, with continuous removal of water using a Dean and Stark trap. When no more water was observed in the toluene layer (3 hours) the mixture was concentrated in vacuo and the residue was taken into methanol (200 cm³) and treated with sodium borohydride (12.0 g) added portionwise over 20 minutes at 0° C. After stirring for 16 hours concentrated hydrochloric acid (10 cm³) was slowly added and the mixture was concentrated in vacuo. The residue was dissolved in water (100 cm³) and basified to pH11 with 5M sodium hydroxide solution. The mixture was extracted with chloroform (3×300 cm³) and the dried (MgSO₄) extracts were evaporated in vacuo. Distillation gave N-[1-(4-pyridyl)ethyl]-1,3-diaminopropane (22.7 g) as a colourless oil, b.p. 108°-114°/0.03 mm.

Also synthesised by a similar method were:
N-[1-(4-pyridyl)ethyl]-1,2-diaminoethane, b.p. 94°-106° C./0.6 mm. and N-[1-(4-pyridyl)prop-1-yl]-1,3-diaminopropane (crude free base, oil).

PREPARATION 6

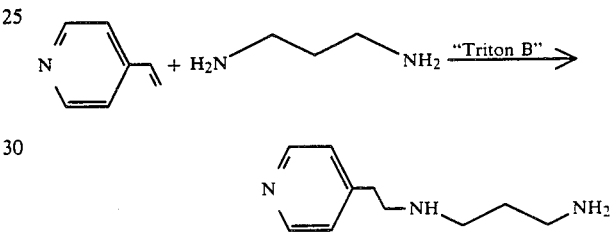

A mixture of 4-vinylpyridine (10.8 cm³), 1,3-diaminopropane (25 cm³) and "Triton B" (Trade Mark) (5 g; 40% solution in water) was stirred and heated at 130° for 20 hours. Water (100 cm³) was added and the mixture was extracted with chloroform (3×100 cm³). The dried (MgSO₄) extracts were evaporated in vacuo to give an oil which was distilled to give 5.4 g of N-[2-(4-pyridyl)ethyl]-1,3-diaminopropane as an oil, b.p. 150°/0.03 mm. (Kugelrohr).

Also synthesized by a similar route were:
N-[2-(4-pyridyl)prop-1-yl]-1,3-diaminopropane (colourless oil, b.p. 150°/0.5 mm (Krugelrohr)), and
N-[2-(4-pyridyl)prop-1-yl]-1,2-diaminoethane (colourless oil, b.p. 160°/0.5 mm) (Kugelrohr).

PREPARATION 7

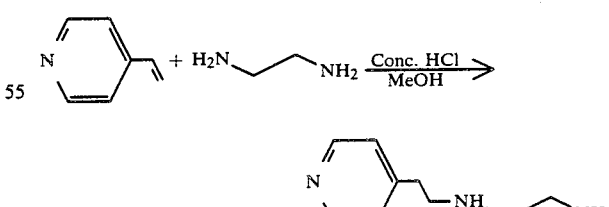

A solution of 4-vinylpyridine (52.5 g) in methanol (250 cm³) was added dropwise over 2 hours to a stirred solution of 1,2-diaminoethane in methanol (500 cm³) and water (500 cm³) under reflux in the presence of an excess of concentrated hydrochloric acid (pH1). After a further 1.5 hours the mixture was concentrated in vacuo and basified to pH9 with 4M sodium hydroxide solution. The solution was extracted with chloroform (4×150 cm³) and the dried (MgSO₄) extracts were evaporated in vacuo to give an oil. Distillation gave N-[2-(4-pyridyl)ethyl]-1,2-diaminoethane as a colourless oil, b.p. 119°–122°/0.09 mm (27.0 g).

PREPARATION 8

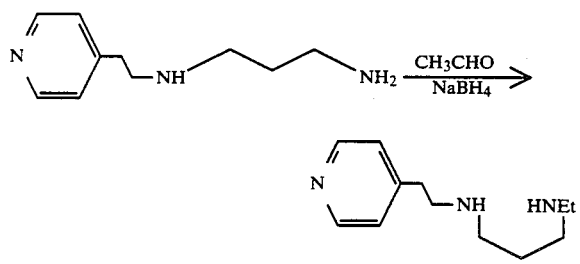

A mixture of N-[2-(4-pyridyl)ethyl]-1,3-diaminopropane (26.4 g), acetaldehyde (7.1 g) and toluene (450 cm³) were heated under reflux with continuous removal of water using a Dean and Stark trap for 2.5 hours. The solvent was then removed in vacuo, methanol (300 cm³) was added and sodium borohydride (12.0 g) was added portionwise to the solution at 0° C. over 0.5 hours. After stirring for 20 hours acetic acid was added slowly until effervescence stopped and the solvent was removed in vacuo. The mixture was basified to pH10 with 4M sodium hydroxide and the solution was extracted with chloroform (3×100 cm³). The dried (MgSO₄) extracts were evaporated to give 1-[2-(4-pyridyl)ethyl]-3-ethyl-1,3-diaminopropane as a crude oil, which was used without purification.

PREPARATION 9

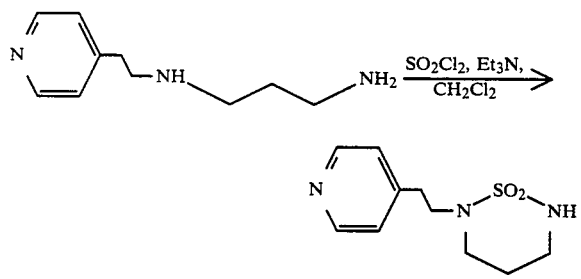

A solution of sulphuryl chloride (7.5 g) in dichloromethane (20 cm³) was added dropwise over 15 minutes to a stirred solution of N-[2-(4-pyridyl)ethyl]-1,3-diaminopropane (10.0 g) in dichloromethane (100 cm³) and triethylamine (11.2 g) at −20°. The mixture was allowed to warm slowly to room temperature over 1 hour. After stirring for 16 hours the solution was filtered and sodium carbonate solution (50 cm³) was added. The aqueous phase was extracted with methylene chloride (2×50 cm³) and the dried (MgSO₄) extracts were evaporated in vacuo to give an oil which was chromatographed on silica ("Merck 60. 9385") eluting with methanol:ethyl acetate, 1:19, to give a solid which was recrystallised from ethanol to afford 2-[2-(4-pyridyl)ethyl] tetrahydro-1,2,6-thiadiazine-1,1-dioxide, m.p. 124°–125° (2.0 g).

Analysis %: Found: C,49.7; H,6.3; N,17.6. Calculated for C₁₀H₁₅N₃O₂S: C,49.8; H,6.4; N,17.4.

Also synthesised by a similar method were:

2-[2-(4-pyridyl)ethyl]-6-ethyltetrahydro-1,2,6-thiadiazine-1,1-dioxide (crude oil);
2-[2-(4-pyridyl)prop-1-yl]tetrahydro-1,2,6-thiadiazine-1,1-dioxide (crude solid);
2-[4-pyridylmethyl]tetrahydro-1,2,6-thiadiazine-1,1-dioxide; m.p. 179°–181°,
Found: C,47.7; H,5.7; N,18.6. Calculated for C₉H₁₃N₃O₂S: C,47.6; H,5.8; N,18.5%
2-[1-(4-pyridyl)ethyl]tetrahydro-1,2,6-thiadiazine-1,1-dioxide; m.p. 184°–5°,
Found: C,50.0; H,6.3; N,17.8. Calculated for C₁₀H₁₅N₃O₂S: C,49.8; H,6.3; N,17.4%
2-[4-pyridylmethyl]-1,2,5-thiadiazolidine-1,1-dioxide (crude solid);
2-[2-(4-pyridyl)prop-1-yl]-1,2,5-thiadiazolidine-1,1-dioxide (crude oil);
2-[1-(4-pyridyl)ethyl]-1,2,5-thiadiazolidine-1,1-dioxide;
2-[2-(4-pyridyl)ethyl]-1,2,5-thiadiazolidine-1,1-dioxide;
2-[1-(4-pyridyl)prop-1-yl]tetrahydro-1,2,6-thiadiazine-1,1-dioxide (crude solid, m.p. 162°–164°);
2-[2-(4-pyridyl)ethyl]-4-methyl-1,2,5-thiadiazolidine-1,1-dioxide and 2-[2-(4-pyridyl)ethyl]-3-methyl-1,2,5-thiadiazolidine-1,1-dioxide as a 3:1 mixture (solid, m.p. 90°–105° ); and
2-[2-(4-pyridyl)prop-1-yl]-4-methyl-1,2,5-thiadiazolidine-1,1-dioxide (crude solid).

PREPARATION 10

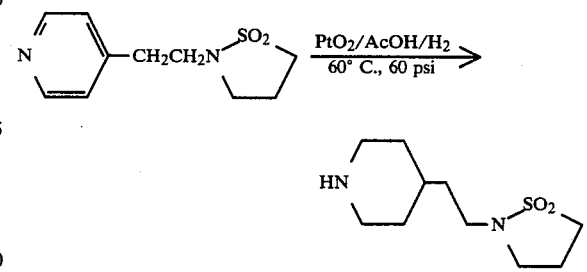

A solution of 2-[2-(4-pyridyl)ethyl]isothiazolidine-1,1-dioxide (12.0 g) in acetic acid (130 cm³) was hydrogenated at 60° and 60 p.s.i. over platinum oxide catalyst until hydrogen uptake ceased. The mixture was filtered through "Solkafloc" (Trade Mark) and the residue concentrated in vacuo. The residual oil was dissolved in chloroform, washed with 5M sodium hydroxide solution, and dried (MgSO₄). Evaporation in vacuo gave an oil (10.4 g). The monooxalate salt of 2-[2-(4-piperidyl)ethyl]isothiazolidine-1,1-dioxide separated from ethyl acetate-methanol, m.p. 151°–152° (9.0 g).

| Analysis %: | |
|---|---|
| Found: | C, 44.7; H, 7.0; N, 8.5. |
| Calculated for C₁₀H₂₀N₂O₂S: (C₂H₂O₄) | C, 44.7; H, 6.9; N, 8.9. |

Also synthesised by a similar method were:
2-[2-(4-piperidyl)ethyl]tetrahydro-1,2-thiazine-1,1-dioxide (crude acetate, oil);
2-[2-(4-piperidyl)prop-1-yl]tetrahydro-1,2-thiazine-1,1-dioxide (crude acetate, oil);
2-[4-piperidylmethyl]isothiazolidine-1,1-dioxide (crude acetate, oil);
2-[2-(4-piperidyl)prop-1-yl]-4-methyl-1,2,5-thiadiazolidine-1,1-dioxide (crude acetate, oil);

and 4-(1-hydroxybut-3-yl)piperidine (crude free base, m.p. 58°–62°).

Also synthesised by a similar method but using ethanol as solvent and hydrogen chloride as the acid instead of acetic acid were:

2-[2-(4-piperidyl)prop-1-yl]isothiazolidine-1,1-dioxide monohydrochloride (m.p. 201°–203° C.);

2-[4-piperidylmethyl]tetrahydro-1,2-thiazine-1,1-dioxide (crude hydrochloride, oil);

2-[1-(4-piperidyl)ethyl]isothiazolidine-1,1-dioxide (crude hydrochloride, oil);

2-[2-(4-piperidyl)ethyl]tetrahydro-1,2,6-thiadiazine-1,1-dioxide monohydrochloride, m.p. 182°–185° C. Found: C,42.1; H,7.8; N,14.3. $C_{10}H_{21}N_3O_2S$. HCl requires: C42.3; H,7.8; N,14.8%;

2-[2-(4-piperidyl)ethyl]-6-ethyltetrahydro-1,2,6-thiadiazine-1,1-dioxide monohydrochloride, m.p. 166°–170° C. Found: C,46.3; H,8.5; N,13.5. $C_{12}H_{25}N_3O_2S$. HCl requires: C,46.2; H,8.4; N,13.5%;

2-[2-(4-piperidyl)ethyl]-1,2,5-thiadiazolidine-1,1-dioxide monohydrochloride, m.p. 167°–174°. Found: C,40.0; H,7.4; N,15.4. $C_9H_{19}N_3O_2S$. HCl requires: C,40.1; H,7.5; N,15.6%;

2-[1-(4-piperidyl)ethyl]tetrahydro-1,2,6-thiadiazine-1,1-dioxide (crush hydrochloride, oil);

2-[4-piperidylmethyl]tetrahydro-1,2,6-thiadiazine-1,1-dioxide (crude hydrochloride, oil);

2-[2-(4-piperidyl)prop-1-yl]tetrahydro-1,2,6-thiadiazine-1,1-dioxide (crude hydrochloride, oil);

2-[4-piperidylmethyl]-1,2,5-thiadiazolidine-1,1-dioxide (crude hydrochloride, oil);

2-[1-(4-piperidyl)ethyl]-1,2,5-thiadiazolidine-1,1-dioxide (crude hydrochloride, oil);

2-[2-(4-piperidyl)prop-1-yl]-1,2,5-thiadiazolidine-1,1-dioxide (crude hydrochloride, oil);

2-[1-(4-piperidyl)prop-1-yl]tetrahydro-1,2,6-thiadiazine-1,1-dioxide (crude hydrochloride, oil);

2-[2-(4-piperidyl)ethyl]-5-methyltetrahydro-1,2,6-thiadiazine-1,1-dioxide crude hydrochloride, solid);

2-(4-piperidylmethyl)-5-methyltetrahydro-1,2,6-thiadiazine-1,1-dioxide (crude hydrochloride, solid); and 2-[2-(4-piperidyl)ethyl]-4-methyl-1,2,5-thiadiazolidine-1,1-dioxide and 2-[2-(4-piperidyl)ethyl]-3-methyl-1,2,5-thiadiazolidine-1,1-dioxide as a 3:1 mixture (crude hydrochloride, oil).

PREPARATION 11

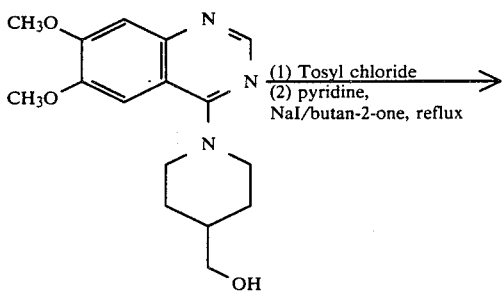

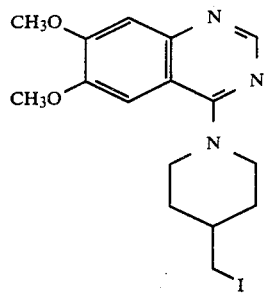

A solution of 6,7-dimethoxy-4-(4-hydroxymethyl-piperidino)quinazoline (3.03 g; Preparation 13) was stirred at 0° in dry pyridine (15 cm³) during the addition of toluene-4-sulphonyl chloride (3.0 g). After 1 hour the mixture solidified, water (100 cm³) was added and stirring was continued for 10 minutes. The solid was filtered and washed with water (50 cm³) and ether (50 cm³). This material (3.5 g) was taken without purification into butan-2-one (150 cm³) and heated under reflux with sodium iodide (10.0 g) for 6 hours. The mixture was cooled, filtered and then concentrated in vacuo. The residue was taken into water (50 cm³) and extracted with chloroform (3×40 cm³). The dried (MgSO₄) extracts were evaporated to give an oil which was chromatographed on silica ("Merck 60. 9385") eluting with methanol:ethyl acetate, 1:49, to afford 1-(6,7-dimethoxyquinazolin-4-yl)-4-(iodomethyl)piperidine as a white solid, m.p. 180°–182° (3.1 g).

Analysis %: Found: C,46.7; H,4.9; N,10.2. Calculated for $C_{16}H_{20}N_3O_2I$: C,46.6; H,4.9; N,10.2.

Also synthesised by a similar method was 1-(6,7-dimethoxyquinazolin-4-yl)-4-(3-iodoprop-1-yl)piperidine, m.p. 120°–122°.

Analysis %: Found: C,49.1; H,5.4; N,9.0; Required for $C_{18}H_{24}N_3O_2I$: C,50.0; H, 5.5; N,9.5.

1-(6,7-Dimethoxyquinazolin-4-yl)-4-(1-iodo-but-3-yl) piperidine was also prepared similarly but was not characterised further.

PREPARATION 12

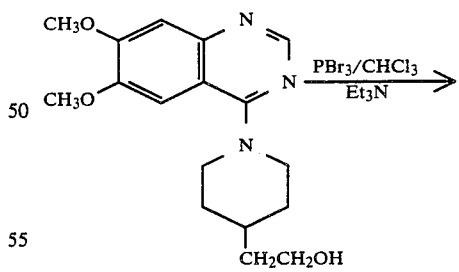

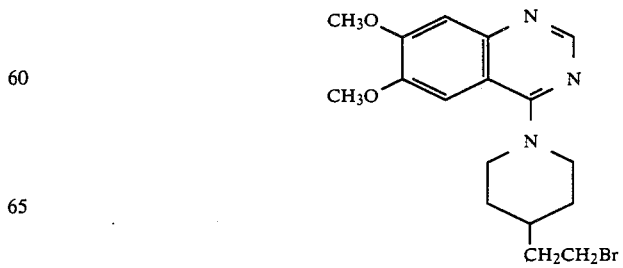

Phosphorus tribromide (9.7 g) was added at room temperature to a stirred solution of 1-(6,7-dimethoxyquinazolin-4-yl)-4-(2-hydroxyethyl)piperidine (7.5 g) in ethanol free chloroform (200 cm³) and triethylamine (5.0 cm³). After stirring for 16 hours the volatile material was removed in vacuo and the residue was taken into aqueous sodium carbonate solution and extracted with chloroform (3×50 cm³). The dried (MgSO₄) extracts were evaporated and the residue was chromatographed on "Florisil" (Trade Mark, Hopkin and Williams) eluting with chloroform to afford 1-(6,7-dimethoxyquinazoline-4-yl)-4-(2-bromoethyl) piperidine ¼ H₂O as a white solid, m.p. 191° (5.6 g).

| Analysis %: | |
|---|---|
| Found: | C, 52.8; H, 6.0; N, 10.8. |
| Calculated for C$_{17}$H$_{23}$N$_3$O$_2$Br: 0.25 H$_2$O | C, 53.1; H, 5.9; N, 10.9. |

Also synthesised by a similar method was 1-(6,7-dimethoxyquinazolin-4-yl)-4-(1-bromoprop-2-yl)piperidine, m.p. 135°–6°.

Analysis %: Found: C,54.7, H,6.3; N,10.7. Calculated for C$_{18}$H$_{24}$BrN$_3$O$_2$: C,54.8; H,6.1; N,10.7.

PREPARATIONS 13 TO 16

The following intermediates were prepared similarly to Example 1 using 4-chloro-6,7-dimethoxyquinazoline, triethylamine and the appropriate 4-substituted piperidine:

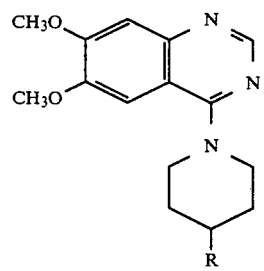

| Preparation No. | R | Form isolated and m.p. (°C.) | Analysis % (Theoretical in brackets) | | |
|---|---|---|---|---|---|
| | | | C | H | N |
| 13 | —CH$_2$OH | Free base 147–148.5° | 63.3 (63.3 | 6.9 7.0 | 13.8 13.8) |
| 14 | —(CH$_2$)$_3$OH | Free base, 108–9° | 65.3 (65.2 | 7.7 7.6 | 12.9 12.7) |
| 15 | —CH(CH$_3$)CH$_2$OH | Free base, 151–2° | 64.7 (65.2 | 7.6 7.6 | 12.8 12.7) |
| 16 | —CH(CH$_3$)CH$_2$CH$_2$OH | Monohydrochloride, 210–212° | 60.1 (59.8 | 7.3 7.4 | 11.1 11.0) |
| 17 | —CH$_2$CH(CH$_3$)OH | Free base, 144–5° | 65.3 (65.2 | 7.6 7.6 | 12.6 12.7) |

PREPARATION 18

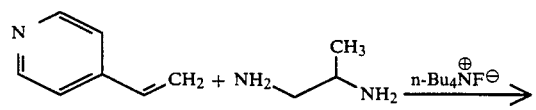

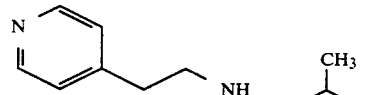

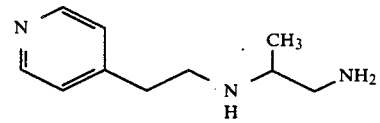

A mixture of 4-vinylpyridine (30 ml), 1,2-diaminopropane (100 ml) and tetrabutylammonium fluoride (10 ml; 1M in T.H.F.) was heated under reflux for 20 hours. Distillation of the residue gave a mixture (approximately 3:1 by n.m.r.) of 1-[N-{2-(4-pyridyl)ethyl}amino]-2-aminopropane and 2-[N-{2-(4pyridyl)ethyl}amino]-1-aminopropane as a mobile oil, b.p. 125°–130°/0.03 mm, (28.0 g).

Also synthesised by a similar method was 1-[N-{2-(4-pyridyl)prop-1-yl}amino]-2-aminopropane, colourless oil, b.p. 120°–122°/0.05 mm.

PREPARATION 19

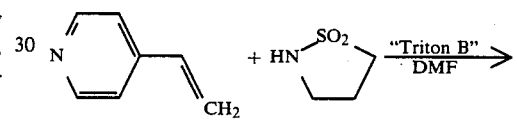

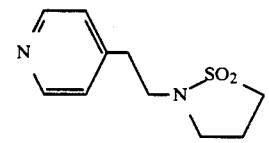

(This is an alternative to the method of Preparation 2).

A mixture of 4-vinylpyridine (324 g), isothiazolidine-1,1-dioxide (373 g), and "Triton B" solution (129 ml, 40% w/v in methanol) was heated in D.M.F. at 50°–55° for 7 hours. The reaction mixture was then concentrated under vacuum, water (2.52 liters) was added, and the product was extracted into CH$_2$Cl$_2$ (3×1.87 liters). The combined methylene chloride extracts were washed with water and then evaporated to dryness. The residue was dissolved in ethyl acetate (1.3 liters) at 35° and hexane (0.87 liters) was added over 10 minutes. The resulting crystalline product was granulated at −5 to 0° for 4 hours, filtered, washed with hexane (0.37 liters) and dried in vacuum at 25°, to give 2-[2-(4-pyridyl)ethyl]isothiazolidine-1,1-dioxide (518 g).

The material was confirmed by n.m.r., i.r. and m.p. to be identical in all respects to the product of Preparation 2.

PREPARATION 20

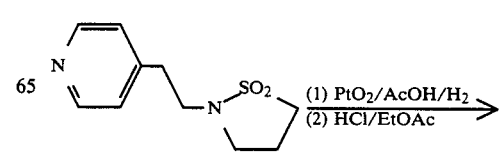

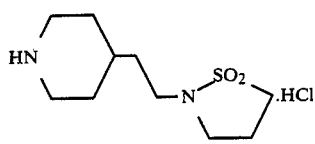

(This is slight alternative to the method of Preparation 10.)

A solution of 2-[2-(4-pyridyl)ethyl)]isothiazolidine-1,1-dioxide (186 g) in acetic acid (2.5 liters) was hydrogenated over platinum oxide catalyst (6.2 g) at 60° and 60 p.s.i. for 3 hours. The catalyst was filtered, the acetic acid solution was evaporated to small volume and the residue was dissolved in chloroform (1.5 liters). The chloroform solution was washed with aqueous sodium hydroxide solution (0.62 liters, 5N) and evaporated to dryness to give the crude product (167.3 g), as the free base.

A sample of the free base (50 g) was dissolved in ethyl acetate (450 ml) and washed with aqueous sodium hydroxide solution (185 ml, 5N). The ethyl acetate solution was concentrated to low volume (150 ml) and a solution of HCl/isopropanol (42 ml, 5.71N) was added over 5 minutes. The resulting product, 2-[2-(4-piperidyl)ethyl]isothiazolidine-1,1-dioxide hydrochloride, was granulated at 0°–5° for 2 hours, filtered and dried in vacuum at 40°–50°, yield 51.4 g, m.p. 191°–193°.

Analysis %: Found: C,44.4; H,7.9; N,10.5; Calculated for $C_{10}H_{20}N_2SO_2 \cdot HCl$ C,44.7; H,7.8; N,10.4.

PREPARATION 21

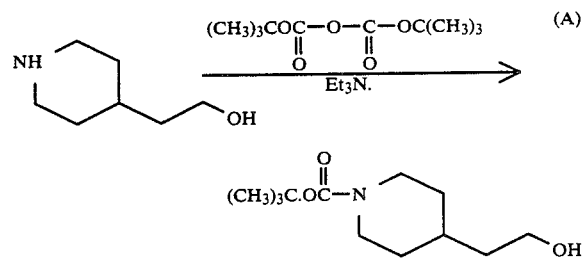

Di-t-butyldicarbonate (52.2 g) was added dropwise at 0° to a stirred solution of 4-(2-hydroxyethyl)-piperidine (30 g) and triethylamine (50 cm³) in dichloromethane (400 cm³). After 3 hours sodium carbonate solution was added, the mixture was separated and the dried (MgSO₄) organic phase was evaporated in vacuo to give an oil which was distilled to afford 1-(t-butyloxycarbonyl)-4-(2-hydroxyethyl)piperidine, b.p. 245°–250°/0.3 mm (Kugelrohr) (33.5 g).

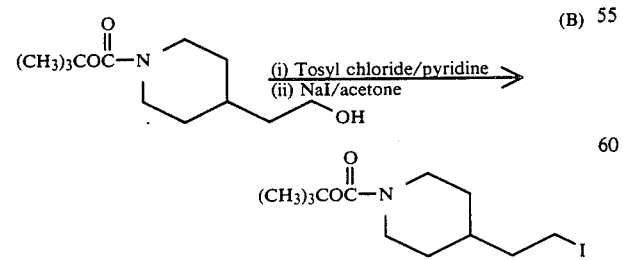

Toluene-p-sulphonylchloride (19.0 g) was added at 0° to a stirred solution of 1-(t-butyloxycarbonyl)-4-(2-hydroxyethyl)piperidine (15.0 g) in dry pyridine (100 cm³). After 16 hours water (20 cm³) was added and the mixture was treated with chloroform (500 cm³) and extracted with water (3×100 cm³). The organic phase was dried (MgSO₄) and evaporated to give an oil (20 g), which was taken into acetone (250 cm³) and heated under reflux for 2 hours with sodium iodide (30.0 g). The mixture was cooled, filtered and evaporated in vacuo to yield an oil which was chromatographed on silica (Merck 60.9385) eluting with chloroform to give 1-(t-butyloxycarbonyl)-4-(2-iodoethyl)piperidine as an oil (10.0 g).

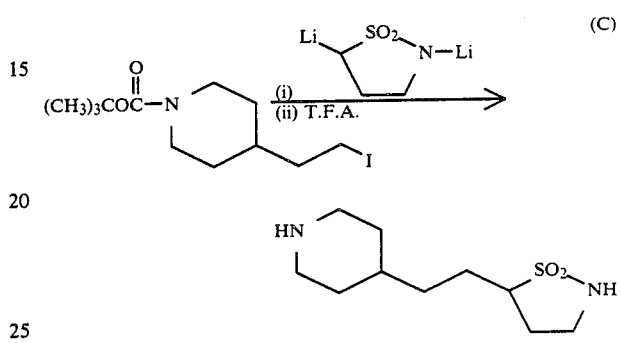

n-Butyl lithium (6.7 cm³ of a 1.5M solution in hexane) was added at −70° to a stirred solution of isothiazolidine-1,1-dioxide (0.605 g) in tetrahydrofuran (25 cm³) under nitrogen. After 10 minutes 1-(t-butyloxycarbonyl)-4-(2-iodoethyl)piperidine (1.7 g) was added, the reaction was allowed to warm up and then stirred for 16 hours. Saturated ammonium chloride was added and the aqueous phase was extracted with chloroform (2×50 cm³), and the dried extracts (MgSO₄) were evaporated to give an oil which was chromatographed on silica (Merck 60.9385) eluting with methanol:chloroform, 1:49, to afford an oil (0.95 g). This material was taken without further purification into trifluoroacetic acid (T.F.A.) (5 cm³) and stirred at room temperature for 2 hours. Volatile material was removed in vacuo to afford 2H-5-[2-(4-piperidyl)ethyl]isothiazolidine-1,1-dioxide as an oil (1.0 g) (crude trifluoroacetate salt), used directly.

PREPARATION 22

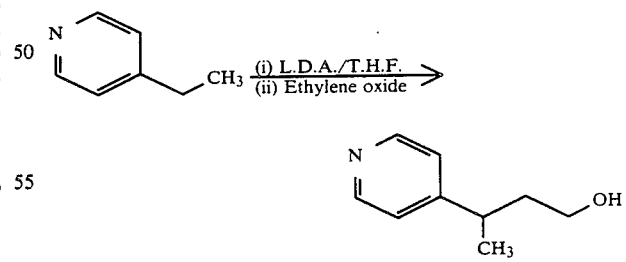

A solution of lithium diisopropylamide [made from n-BuLi (13.3 cm³) and diisopropylamine (2.8 cm³) in T.H.F. (10 cm³)] was added at −70° to a stirred solution of 4-ethylpyridine (2.0 g) in T.H.F. (10 cm³) under nitrogen. After 10 minutes the red solution was treated with ethylene oxide (1 cm³) giving an immediate suspension. After warming to room temperature, water (10 cm³) was added and the phases were separated. The aqueous phase was extracted with chloroform (2×20 cm³) and the combined organic extracts were dried (MgSO₄) and evaporated in vacuo. Chromatography on silica (Merck 60.9385) eluting with methanol: ethyl acetate, 3:20, gave 3-(4-pyridyl)-butan-1-ol as an oil.

PREPARATION 23

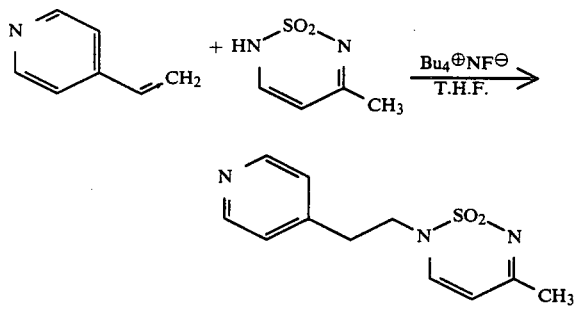

4-Vinylpyridine (3.2 cm³) was added at room temperature to a stirred solution of 2H-5-methyl-1,2,6-thiadiazine-1,1-dioxide (4.38 g) in tetrahydrofuran (8 cm³) and tetrabutylammonium fluoride (0.6 cm³ as a 1M solution in T.H.F.). The mixture solidified after 1 minute and was treated with water (15 cm³) and extracted thoroughly with chloroform (5×20 cm³). The combined extracts were dried (MgSO₄), concentrated in vacuo, and chromatographed on silica (Merck 60.9385) eluting with methanol:chloroform, 1:20, to afford 2-[2-(4-pyridyl)ethyl]-5-methyl-1,2,6-thiadiazine-1,1-dioxide as a yellow solid (2.12 g).

PREPARATION 24

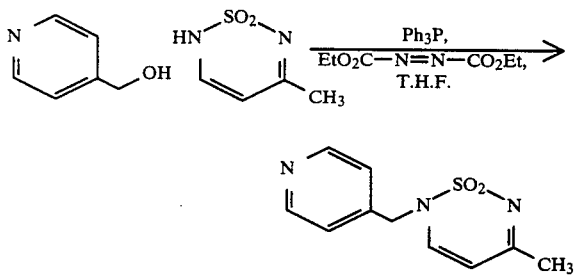

Diethylazodicarboxylate (3.62 g) was added dropwise at room temperature to a stirred mixture of 4-hydroxymethylpyridine (2.08 g), 2H-5-methyl-1,2,6-thiadiazine-1,1-dioxide (3.0 g) and triphenyl phosphine (5.45 g) in tetrahydrofuran (20 cm³) and the mixture was stirred for 48 hours. After concentration in vacuo, the residue was chromatographed on silica (Merck 60.9385) eluting with chloroform to give an oil which was recrystallised from ethyl acetate to afford 2-(4-pyridylmethyl)-5-methyl-1,2,6-thiadiazine-1,1-dioxide as white needles, m.p. 100°–101°, (1.0 g).

Analysis %: Found: C,50.5; H,4.7; N,17.7; Calculated for C₁₀H₁₁N₃O₂S: C,50.2; H,4.6; N,17.6.

Also synthesised by a similar method was 2-(4-pyridylmethyl)-1,2,6-thiadiazine-1,1-dioxide; m.p. 116°–118°.

Analysis %: Found: C,47.6; H,4.2; N,18.7; Calculated for C₉H₉N₃O₂S: C,48.4; H,4.1; N,18.8.

This was then hydrogenated by the method of Preparation 10 but using ethanol as the solvent and hydrogen chloride as the acid to give 2-(4-piperidylmethyl)tetrahydro-1,2,6-thiadiazine-1,1-dioxide (crude hydrochloride, oil).

PREPARATION 25

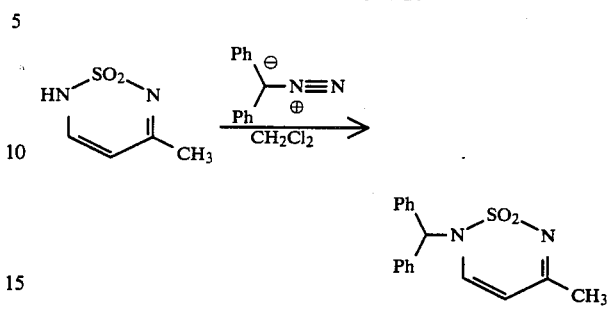

A solution of diphenyldiazomethane [prepared from Nickel peroxide (4 g) and benzophenone hydrazone (2.0 g) in dichloromethane (20 cm³)] was added dropwise at 0° to a stirred solution of 5-methyl-1,2,6-thiadiazine-1,1-dioxide (1.46 g) in dichloromethane (50 cm³). The red colour was immediately discharged and nitrogen evolution was visible. After stirring for ½ hour the solvents were removed in vacuo and the residue was chromatographed on silica (Merck 60.9385) eluting with chloroform to give a solid (1.2 g) which was recrystallised from ethyl acetate to afford 1,1-dioxo-2-benzhydryl-5-methyl-1,2,6-thiadiazine as white microcrystals, m.p. 174°–177° (0.74 g).

Analysis %: Found: C,65.1; H,5.2; N,9.0; Calculated for C₁₇H₁₆N₂O₂S: C,65.4; H,5.2; N,9.0.

ACTIVITY DATA

Test Method

The following accurately describes the test procedures carried out in anaesthetised dogs to evaluate the compounds for cardiac stimulant activity. The left ventricular pressure (LVP) of a Nembutal anaesthetised (30 mg/kg, intravenous) male or female beagle dog is measured by means of a Millar transducer introduced into the left ventricle via the left common carotid artery. A Devices 4-channel chart recorded is used to record the left ventricular pressure, and a differentiator is used to derive the maximum rate of change of left ventricular pressure from LVP upon administration of the test compound. The test compound, dissolved in an inert solvent, is in fact given by injection into the femoral vein. The maximum rate of change of the left ventricular pressure (dp/dt [max.]) is a measure of the maximum percentage increase in cardiac contractility (force of cardiac contraction) effected by the test compound. Because each dog may vary in its level of response to a cardiac stimulant, each test result should be compared to the result obtained in the same dog with the known cardiac stimulant 4-(4-{3-n-butylureido}- piperidino)-6,7-dimethoxyquinazoline, generically known as buquineran, which is the subject of Example 1of U.S. Pat. No. 4,001,422. This known cardiac stimulant in a suitable solvent is also injected into the femoral vein and the result recorded as above, and this quinazoline is administered to the dog at least 30 minutes before the administration of the test compound.

Using the stated test method the following results were obtained:

| Product of Example No. | Maximum percentage increase in cardiac contractility effected by the test compound at the stated dose level. | Corresponding result obtained in the same dog with the known cardiac stimulant buquineran at 0.25 mg./kg. |
|---|---|---|
| 1 | 111% at 0.25 mg./kg. | 19% |
| 2 | 56% at 0.25 mg./kg. | 27% |
| 3 | 70% at 0.25 mg./kg. | 17% |
| 4 | 46% at 0.05 mg./kg. | 29% |
| 5 | 85% at 0.25 mg./kg. | 26% |
| 6 | 108% at 0.25 mg./kg. | 43% |
| 7 | 25% at 0.25 mg./kg. | 45% |
| 8 | 48% at 0.25 mg./kg. | 35% |
| 9 | 65% at 0.25 mg./kg. | 24% |
| 10 | 76% at 0.25 mg./kg. | 26% |
| 11 | 120% at 0.25 mg./kg. | 42% |
| 12 | 43% at 0.25 mg./kg. | 21% |
| 13 | 46% at 0.25 mg./kg. | 20% |
| 14 | 70% at 0.25 mg./kg. | 27% |
| 15 | 125% at 0.25 mg./kg. | 39% |
| 16 | 96% at 0.25 mg./kg. | 33% |
| 17 | 29% at 0.05 mg./kg. | 33% |
| 18 | 18% at 0.05 mg./kg. | 29% |
| 19 | 32% at 0.05 mg./kg. | 39% |
| 20 | 94% at 0.25 mg./kg. | 38% |
| 21 | 46% at 0.05 mg./kg. | 31% |
| 22 | 46% at 0.05 mg./kg. | 25% |
| 23 | 88% at 0.25 mg./kg. | 21% |
| 24 | 25% at 0.05 mg./kg. | 43% |
| 25 | 21% at 0.05 mg./kg. | 28% |
| 26 | 17% at 0.05 mg./kg. | 46% |
| 27 | 30% at 0.05 mg./kg. | 30% |
| 28 | 26% at 0.05 mg./kg. | 46% |
| 29 | 22% at 0.05 mg./kg. | 26% |
| 30 | 37% at 0.05 mg./kg. | 37% |
| 31 | 67% at 0.25 mg./kg. | 29% |
| 32 | 33% at 0.05 mg./kg. | 58% |
| 33 | 88% at 0.05 mg./kg. | 60% |
| 34 | 71% at 0.05 mg./kg. | 32% |
| 35 | 109% at 0.05 mg./kg. | 35% |
| 36 | 64% at 0.25 mg./kg. | 45% |
| 37 | 56% at 0.05 mg./kg. | 33% |
| 38 | 38% at 0.05 mg./kg. | 35% |
| 39 | 69% at 0.05 mg./kg. | 33% |
| 40 | 55% at 0.05 mg./kg. | 35% |
| 41 | 62% at 0.05 mg./kg. | 30% |
| 42 | 76% at 0.05 mg./kg. | 58% |
| 43 | 33% at 0.05 mg./kg. | 28% |
| 44 | 19% at 0.05 mg./kg. | 23% |
| 45 | 30% at 0.05 mg./kg. | 31% |
| 46 | 21% at 0.25 mg./kg. | 25% |
| 47 | 25% at 0.05 mg./kg. | 25% |

We claim:

1. A quinazoline compound of the formula:

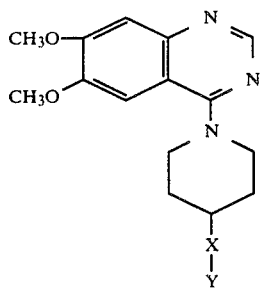

or a pharmaceutically acceptable salt thereof; wherein

X is a straight or branched chain alkylene group having a total of from 1 to 4 carbon atoms; and Y is a group of the formula:

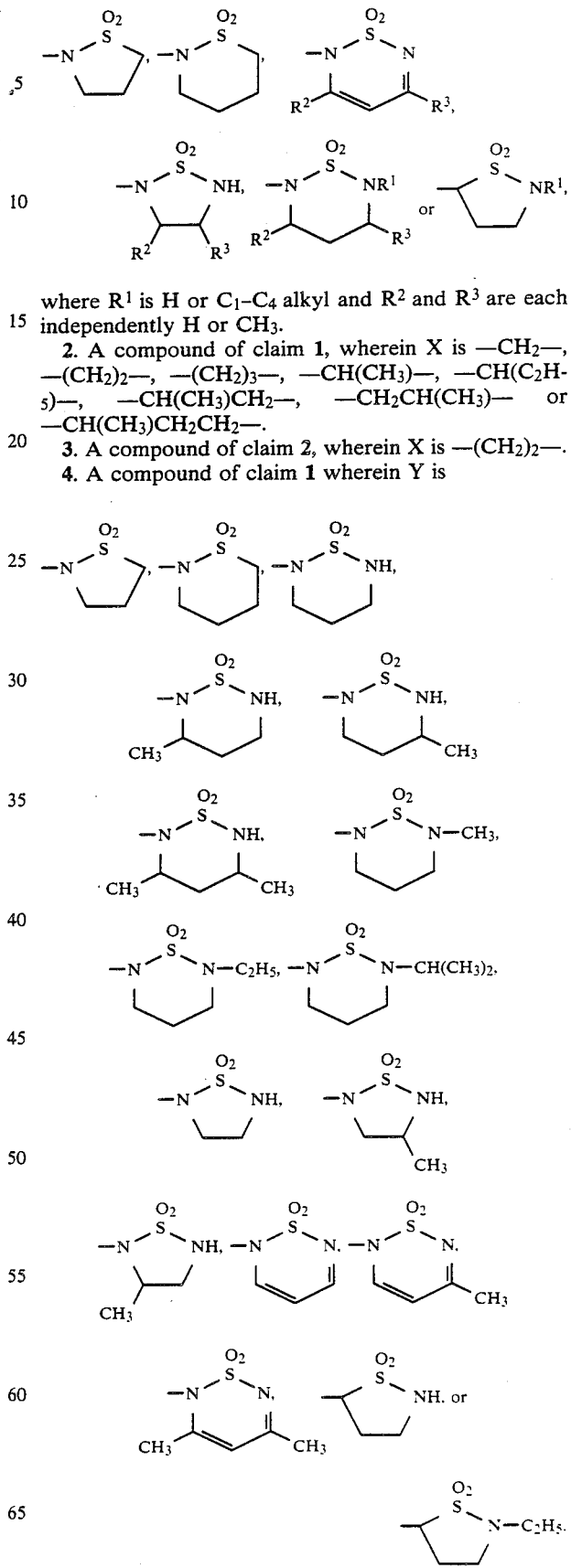

where $R^1$ is H or $C_1$-$C_4$ alkyl and $R^2$ and $R^3$ are each independently H or $CH_3$.

2. A compound of claim 1, wherein X is —CH$_2$—, —(CH$_2$)$_2$—, —(CH$_2$)$_3$—, —CH(CH$_3$)—, —CH(C$_2$H$_5$)—, —CH(CH$_3$)CH$_2$—, —CH$_2$CH(CH$_3$)— or —CH(CH$_3$)CH$_2$CH$_2$—.

3. A compound of claim 2, wherein X is —(CH$_2$)$_2$—.

4. A compound of claim 1 wherein Y is

5. A compound of claim 4, wherein X is —CH₂—, —(CH₂)₂—, —(CH₂)₃—, —CH(CH₃)—, —CH(C₂H₅)—, —CH(CH₃)CH₂—, —CH₂CH(CH₃)— or —CH(CH₃)CH₂CH₂—.

6. A compound of claim 5, wherein X is —(CH₂)₂—.

7. A compound of claim 5, wherein Y is

[structures]

8. A compound of claim 6, wherein Y is

[structures]

9. The compound of claim 8 wherein Y is

[structure]

10. The compound of claim 8 wherein Y is

[structure]

11. The compound of claim 8 wherein Y is

[structure]

12. The compound of claim 11 in the form of its pharmaceutically acceptable HCl salt.

13. A composition for stimulating the heart comprising a heart-stimulating effective amount of a compound of claim 1 together with a pharmaceutically acceptable diluent or carrier.

14. A method of stimulating the heart of an animal, including man, in need of such heart-stimulation, which comprises administering to said animal a heart stimulating amount of a quinazoline compound of the formula:

[structure]

or a pharmaceutically acceptable salt thereof; wherein
x is a straight or branched chain alkylene group having a total of from 1 to 4 carbon atoms; and
Y is a group of the formula:

[structures with R¹, R², R³]

where R¹ is H or C₁–C₄ alkyl and R² and R³ are each independently H or CH₃.

15. A method of claim 14, wherein X is —CH₂—, —(CH₂)₂—, —(CH₂)₃—, —CH(CH₃)—, —CH(C₂H₅)—, —CH(CH₃)CH₂—, —CH₂CH(CH₃)— or —CH(CH₃)CH₂CH₂—.

16. A method of claim 15, wherein X is —(CH₂)₂—.

17. A method of claim 14 wherein Y is

[structures]

[chemical structures]

18. A method of claim 17, wherein X is —CH₂—, —(CH₂)₂—, —(CH₂)₃—, —CH(CH₃)—, —CH(C₂H₅)—, —CH(CH₃)CH₂—, —CH₂CH(CH₃)— or —CH(CH₃)CH₂CH₂—.

19. A method of claim 18, wherein X is —(CH₂)₂—.

20. A method of claim 18, wherein Y is

[chemical structures]

21. A method of claim 19, wherein Y is

[chemical structures]

22. The method of claim 21 wherein Y is

[chemical structure]

23. The method of claim 21 wherein Y is

[chemical structure]

24. The method of claim 21 wherein Y is

[chemical structure]

25. The method of claim 24 wherein the compound is in the form of its pharmaceutically acceptable HCl salt.